(12) United States Patent
Fu

(10) Patent No.: US 6,565,829 B2
(45) Date of Patent: May 20, 2003

(54) 5-ARYLSULFONYL INDOLES USEFUL FOR TREATING DISEASE

(75) Inventor: Jian-Min Fu, Kalamazoo, MI (US)

(73) Assignee: Pharmacia & Upjohn Company, Kalamazoo, MI (US)

( * ) Notice: Subject to any disclaimer, the term of this patent is extended or adjusted under 35 U.S.C. 154(b) by 0 days.

(21) Appl. No.: 10/210,377

(22) Filed: Aug. 1, 2002

(65) Prior Publication Data

US 2003/0060498 A1 Mar. 27, 2003

Related U.S. Application Data

(60) Provisional application No. 60/326,885, filed on Oct. 3, 2001, and provisional application No. 60/309,832, filed on Aug. 3, 2001.

(51) Int. Cl.[7] .................. A61K 51/00; A61M 36/14
(52) U.S. Cl. ............... 424/1.89; 424/1.11; 424/1.65; 424/1.81; 424/1.85; 424/9.1; 424/9.3; 424/9.2; 548/400; 548/414; 548/416; 514/183; 514/410
(58) Field of Search .................. 424/1.11, 1.65, 424/1.81, 1.85, 1.89, 9.1, 9.2, 9.3, 9.37; 548/402, 414, 416; 514/183, 359, 408, 410

(56) References Cited

U.S. PATENT DOCUMENTS 5,637,593 A    6/1997   Porter et al. ............... 514/274
6,187,805 B1   2/2001   Pineiro et al. ............. 514/415

FOREIGN PATENT DOCUMENTS

| WO | WO94/14770 | 7/1994 |
| WO | WO99/43654 | 9/1999 |
| WO | WO01/05793 | 1/2001 |
| WO | WO 01/05793 | 2/2001 |
| WO | WO 02/078693 | * 10/2002 |

OTHER PUBLICATIONS

"5–$HT_6$ Serotonin Receptor Binding of Indolealkylamines: A Preliminary Structure–Affinity Investigation", Richard A. Glennon, et al.; Medicinal Chemistry Research (1999), pp. 108–117 (10 sheets).

"2–Substituted Tryptamines: Agents with Selectivity for 5–$HT_6$ Serotonin Receptors", Richard A. Glennon, et al.; Journal of Medicinal Chemistry, American Chemical Society, vol. 43, No. 5 (2000), pp. 1011–1018 (8 sheets).

* cited by examiner

Primary Examiner—Dameron L. Jones
(74) Attorney, Agent, or Firm—Mary J. Hosley

(57) ABSTRACT

The invention provides derivatives of 5-arylsulfonyl indole and 5-arylsulfonyl indoline compounds which may be in the form of pharmaceutical acceptable salts or compositions that are useful in treating central nervous system diseases such as anxiety and depression. The invention also includes intermediates and processes to make the compounds, isotopically-labeled forms of the compounds and the use of the isotopically labeled forms of the compounds to perform nuclear magnetic resonance imaging and positron emission tomography.

46 Claims, No Drawings

5-ARYLSULFONYL INDOLES USEFUL FOR TREATING DISEASE

CROSS REFERENCE TO RELATED APPLICATIONS

This application claims the benefit of U.S. provisional application Ser. No. 60/309,832 filed on Aug. 3, 2001, under 35 USC 119(e)(i) and U.S. provisional application Ser. No. 60/326,885 filed on Oct. 3, 2001, under 35 USC 119(e)(i), which are incorporated herein by reference in their entirety.

BACKGROUND OF THE INVENTION

1. Field of the Invention

The present invention relates to substituted 5-arylsulfonyl indoles and indolines which interact with serotonin receptors, such as $5-HT_6$ receptors, and are useful for treating anxiety, depression, schizophrenia, stress-related disorders such as irritable bowel syndromes panic, a phobia, obsessive compulsive disorder, obesity, post-traumatic stress syndrome, epilepsy, and other central nervous system (CNS) disorders in humans and animals.

The major classes of serotonin receptors ($5-HT_{1-7}$) contain fourteen to eighteen separate receptors that have been formally classified. See Glennon, et al., Neuroscience and Behavioral Reviews, 1990, 14, 35; and D. Hoyer, et al. Pharmacol. Rev. 1994, 46, 157–203. There is currently a need for pharmaceutical agents that are useful to treat diseases and conditions that are associated with 5-HT receptors. In particular, there is a need for agents that can selectively bind to individual receptor sub-types (e.g. receptor-specific agonists or antagonists); such agents would be useful as pharmaceutical agents, or would be useful to facilitate the study of the 5-HT receptor family, or to aid in the identification of other compounds that selectively bind to the specific 5-HT receptors.

For example, the $5-HT_6$ receptor was identified in 1993 (Monsma et al. Mol. Pharmacol. 1993, 43, 320–327 and Ruat, M. et al. Biochem. Biophys. Res. Com. 1993, 193, 269–276). Several antidepressants and atypical antipsychotics bind to the $5-HT_6$ receptor with high affinity and this binding may be a factor in their profile of activities (Roth et al. J. Pharm. Exp. Therapeut. 1994, 268, 1403–1410; Sleight et al. Exp. Opin. Ther. Patents 1998, 8, 1217–1224; Bourson et al. Brit. J. Pharm. 1998, 125, 1562–1566; Boess et al. Mol. Pharmacol. 1998, 54, 577–583; Sleight et al. Brit. J. Pharmacol. 1998, 124, 556–562). In addition, the $5-HT_6$ receptor has been linked to generalized stress and anxiety states (Yoshioka et al. Life Sciences 1998, 17/18, 1473–1477). Together these studies and observations suggest that compounds that antagonize the $5-HT_6$ receptor will be useful in treating disorders of the central nervous system, such as anxiety, depression, schizophrenia, stress-related disorders such as irritable bowel syndrome, panic, a phobia, obsessive compulsive disorder, obesity, post-traumatic stress syndrome, and epilepsy. In general, compounds of formula I exhibit selective inhibition of $5-HT_6$ serotonin receptors relative to the inhibition of other 5-HT serotonin receptors.

General anxiety disorder (GAD) occurs when a person worries about things such as family, health, or work when there is no reason to worry and is unable not to worry. About 3 to 4% of the U.S. population has GAD during the course of a year. GAD most often strikes people in childhood or adolescence, but can begin in adulthood, too. It affects women more often than men. Currently, treatment involves cognitive-behavioral therapy, relaxation techniques, and biofeedback to control muscle tension and medications such as benzodiazepines, imipramine, and buspirone. These drugs are effective but all have side-effect liabilities. Therefore, there is a need of a pharmaceutical agent to address the symptoms with fewer side effects.

Depression is a mood disorder of varying lengths of normally several months to more than two years and of varying degrees of feelings involving sadness, despair, and discouragement. The heterocyclic antidepressants (HCA's) are currently the largest class of antidepressants, but monoamine oxidase inhibitors (MAOI's) are used in particular types of depression. Common side effects from HCA's are sedation and weight gain. In elderly patients with organic brain disease, the side effects from HCA's can also include seizures and behavioral symptoms. The main side effects from using MAOI's occur from dietary and drug interactions. Therefore, agents with fewer side effects would be useful.

Schizophrenia is a disease having multiple aspects. Currently available drugs are generally aimed at controlling the positive aspects of schizophrenia, such as delusions. One drug, Clozapine, is aimed at a broader spectrum of symptoms associated with schizophrenia. This drug has many side effects and is thus not suitable for many patients. Thus, there is a need for a drug to treat the cognitive and attention deficits associated with schizophrenia. Similarly, there is a need for a drug to treat the cognitive and attention deficits associated with schizoaffective disorders, or similar symptoms found in the relatives of schizophrenic patients.

Post-traumatic stress disorder (PTSD) is a form of anxiety triggered by memories of a traumatic event that directly affected the patient or that the patient may have witnessed. The disorder commonly affects survivors of traumatic events including sexual assault, physical assault, war, torture, natural disasters, an automobile accident, an airplane crash, a hostage situation, or a death camp. The affliction also can affect rescue workers at an airplane crash or a mass shooting, someone who witnessed a tragic accident or someone who has unexpectedly lost a loved one. Treatment for PTSD includes cognitive-behavioral therapy, group psychotherapy, and medications such as Clonazepam, Lorazepam and selective serotonin-reuptake inhibitors such as Fluoxetine, Sertraline, Paroxetine, Citalopram and Fluvoxamine. These medications help control anxiety as well as depression. Various forms of exposure therapy (such as systemic desensitization and imaginal flooding) have all been used with PTSD patients. Exposure treatment for PTSD involves repeated reliving of the trauma, under controlled conditions, with the aim of facilitating the processing of the trauma. Therefore, there is a need for better pharmaceutical agents to treat post-traumatic stress disorder.

Stress may increase the release of epinephrine from the adrenal medulla and norepinephrine from adrenergic neurons activated by central nervous system (CNS) stimulation. High levels of circulating epinephrine mediate alpha-adrenergic effects including increases in heart rate and cardiac output. Epinephrine may also be taken up by $beta_2$ receptors on the presynaptic neuronal membrane and may enhance release of norepinephrine from storage granules. Transient epinephrine surges resulting from stress may produce considerably more prolonged vasoconstriction. Stress-induced activation of the sympathetic nervous system may lead to hypertension. Stress also can cause stress gastritis and affect the efficacy of medical treatment in some ulcer patients. There is a need for pharmaceutical agents to treat stress-related diseases.

Panic disorders, phobias, and obsessive compulsive behavior are forms of neurosis. They are all related to excessive anxiety. All humans experience fear and anxiety in response to an external threat, or a difficult situation. However, the neuroses noted above, are abnormal responses to ordinary situations. The causes of such neurotic disorders are not fully known.

Anxiety can arise suddenly, as in panic, or gradually over many minutes, hours, or even days. Anxiety may last for variable periods of time ranging from less than a minute to years. Brief panic attacks are common. However, most persons recover without treatment, and panic disorder is much less common.

Phobias are similar to panic attacks in that they involve anxiety. However, in the various phobias the anxiety is not the free-floating anxiety of panic disorder, but instead focuses on specific situations or stimuli. Persons who have a phobia often realize that their anxiety is excessive, but nonetheless, they tend to avoid the situations or stimuli that disturb them. If they must be exposed to such situations or stimuli they endure them with great distress. Some relatively commonly observed phobias include agoraphobia, that is, the fear of being trapped in closed places, fear of snakes, fear of heights, fear of the dark, fear of strangers, fear of storms, fear of water, heights, and fear of flying.

Persons suffering from an obsessive-compulsive disorder feel compelled to perform repetitive, purposeful, rituals to control their obsessions. For example, a person with an obsessive fear of contamination might compensate with excessive hand washing.

These panic and anxiety disorders may be treated with behavior therapy and antidepressants and benzodiazepines. Obsessive compulsive disorders may be treated with behavior therapy and various drugs such as serotonin reuptake inhibitors (SRIs), selective serotonin reuptake inhibitors (SSRIs—e.g., fluoxetine, fluvoxamine, paroxetine, sertraline), and clomipramine (a tricyclic antidepressant). Augmentation with haloperidol, or atypical antipsychotics may be effective. However, these drugs, especially the benzodiazepines and the antipsychotics, have potentially serious side effects. Therefore, there is a need for a pharmaceutical agent to treat these conditions.

Epilepsy is a recurrent, paroxysmal disorder of cerebral function characterized by sudden, brief attacks of altered consciousness, motor activity, sensory phenomena, or inappropriate behavior caused by excessive discharge of cerebral neurons. Treatment aims primarily to control seizures. A causative disorder may need to be treated as well. No single drug controls all types of seizures, and different drugs are required for different patients. Patients rarely require several drugs. Commonly used drugs include phenytoin, carbamazepine, or valproate gabapentin, lamotrigine, and topiramate. Therefore, there is a need for a pharmaceutical agent to treat epilepsy.

Traditionally, obesity has been defined as a body weight of >30% above ideal or desirable weight on standard height-weight tables. Currently, obesity is usually defined in terms of the body mass index (BMI)—weight (in kilograms) divided by the square of the height (in meters). The general cause of obesity is simple—expending less energy than is consumed. However, how people regulate body weight, primarily body fat, is still elusive and not fully understood. Typically, the determinants of obesity are divided into three categories: genetic, environmental, and regulatory. Recent genetic discoveries have helped explain how genes may determine obesity and how they may influence the regulation of body weight. Scientific studies estimate that genetics may account for about 33% of the variation in body weight. The remaining variation may be caused by environmental and regulatory factors. Environmental factors include socioeconomic status, large food intake, and sedentary lifestyle. Regulatory factors include pregnancy, endocrine, and psychological influences. Despite the analysis of obesity in terms of these three factors, the final common pathway to caloric balance lies in behavior mediated by the CNS. Recent attempts at pharmacotherapy of obesity has lead to widespread valvular heart disease in patients who received fenfluramine alone or in combination with phentermine (often referred to as fen-phen). Therefore, there is a need for a pharmaceutical agent to treat obesity.

General CNS diseases to be treated by the compounds of the present invention include cognitive disorders such as mild cognitive impairment, Alzhiemer's disease, and attention deficit disorder with or without hyperactivity. Alzheimer's disease (AD) is a complex disease related with age that slowly progresses to loss of memory and language skills, with the related problems of having difficulties in learning and making decisions and judgments. Approximately 4 million Americans are reported to be suffering from AD. Currently available drugs, tacrine, donepezil and rivostigmine, are used to only retard the progression of the disease. The above-mentioned drugs are to enhance the cholinergic transmission. However, these drugs have serious side effects. There is a need for a drug to treat AD more effectively and have fewer side effects. Meneses, A., Drug News Perspect., 2001, 14, 396–400.

2. Description of the Related Art

U.S. Pat. No. 5,637,593 and its foreign counterpart WO 94/14770 discloses tryptamine analogues that act as 5-HT1-like agonists. The compounds are expected to have utility in the treatment and/or prophylaxis of migraine, and other conditions associated with cephalic pain, such as cluster headache, headache associated with vascular disorders, and other neuralgia. They are also expected to have utility in the treatment or prophylaxis of portal hypertension.

WO 01/05793 discloses 9-arylsulfone-1,2,3,4,5,6-hexahydroazepino[4,5-]indoles which are useful in treating anxiety, depression, schizophrenia, stress related disease, panic, a phobia, obsessive compulsive disorder, obesity, and post-traumatic stress syndrome, in humans and animals.

WO 99/43654 discloses substituted indoles, and substituted idolines that act as are useful as inhibitors of phospholipase enzymes and are useful in treating or preventing inflammatory conditions in mammals.

SUMMARY OF INVENTION

In general, the present invention provides compounds of Formula I

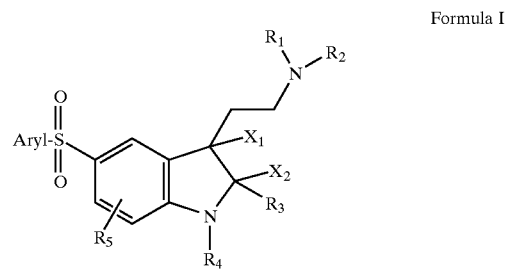

Formula I wherein
Aryl is phenyl, naphthyl, hetereoaromatic, substituted phenyl, substituted naphthyl, or substituted heteroaromatic;

$X_1$ and $X_2$ are both H or together form a bond between the C2 and the C3 carbon of the indole-ring of Formula I;

$R_1$ is H, $C_1$–$C_6$ alkyl, substituted alkyl, aryl, or —C(O)O-t-butyl;

$R_2$ is H, $C_1$–$C_6$ alkyl, substituted alkyl, aryl, or —C(O)O-t-butyl, provided that only one of $R_1$ and $R_2$ is —C(O)O-t-butyl;

$R_3$ is H, halogen, $C_1$–$C_6$ alkyl, substituted alkyl, or aryl;

$R_4$ is H, $C_1$–$C_6$ alkyl, substituted alkyl, or aryl;

Provided that $R_3$ and $R_4$ may not both be H;

$R_5$ is hydrogen, halogen, $C_1$–$C_4$ alkyl, substituted alkyl, —O—$C_1$–$C_6$ alkyl, substituted —O—$C_1$–$C_6$ alkyl, CN, $NO_2$, OH, —$N_3$, $NR_1R_2$, —C(O)$NR_1R_2$, —C(S)$NR_1R_2$, —O-aryl, or aryl;

and pharmaceutically acceptable salts thereof. They are useful for treating anxiety, depression, schizophrenia, stress-related disorders such as irritable bowel syndrome, panic, a phobia, obsessive compulsive disorder, obesity, post-traumatic stress syndrome, epilepsy, and other central nervous system (CNS) disorders in humans and animals, including cognitive disorders such as mild cognitive impairment, Alzhiemer's disease, and attention deficit disorder with or without hyperactivity.

The invention also provides a method for treating a disease or condition in a mammal, wherein the 5-$HT_6$ receptor is implicated, comprising administering to a mammal a therapeutically effective amount of the compound of Formula 1. The invention further provides intermediates and processes to make the final compounds.

The invention still further provides isotopically-labeled compounds, which are identical to those recited in Formula 1, but for the fact that one or more atoms are replaced by an atom having an atomic mass or mass number different from the atomic mass or mass number usually found in nature and means for using the isotopically labeled compounds in the performance of positron emission tomography and nuclear magnetic resonance imaging.

DETAILED DESCRIPTION OF THE INVENTION

Formula I wherein

Aryl is phenyl, naphthyl, hetereoaromatic, substituted phenyl, substituted naphthyl, or substituted heteroaromatic;

$X_1$ and $X_2$ are both H or together form a bond between the C2 and the C3 carbon of the indole-ring of Formula I;

$R_1$, is H, $C_1$–$C_6$ alkyl, substituted alkyl, aryl, or —C(O)O-t-butyl provided that only one of $R_1$ and $R_2$ is —C(O)O-t-butyl;

$R_2$ is H, $C_1$–$C_6$ alkyl, substituted alkyl, aryl, or —C(O)O-t-butyl, provided that only one of $R_1$ and $R_2$ is —C(O)O-t-butyl;

Substituted alkyl is an alkyl moiety having from 1–6 carbon atoms, 0–3 substituents independently selected from —F, —Cl, —Br, and —I, and 0–1 substituent selected from —$OR_{1-0}$, —$SR_{1-0}$, —$NR_{1-0}R_{1-0}$, —C(O)$R_{1-0}$, —C(O)$NR_{1-0}R_{1-0}$, —CN, —$NR_{1-0}$C(O)$R_{1-0}$, —S(O)$_2NR_{1-0}R_{1-0}$, —$NR_{1-0}$S(O)$_2R_{1-0}$, —$NO_2$, and aryl;

Each $R_{1-0}$ is independently selected from —H, $C_1$–$C_6$ alkyl, cycloalkyl, heterocycloalkyl, halogenated alkyl, halogenated cycloalkyl, halogenated heterocycloalkyl, or aryl;

Cycloalkyl is a cyclic ring moiety having from 3–6 carbon atoms;

Heterocycloalkyl is a cyclic ring moiety having from 4–7 atoms with 1–2 atoms within the ring selected from N, O, and S;

Halogenated alkyl is an alkyl moiety having from 1–6 carbon atoms and 1 to (2n+1) substituent(s) independently selected from —F, —Cl, —Br, and —I, where n is the maximum number of carbon atoms in the moiety;

Halogenated cycloalkyl is a cyclic ring moiety having from 3–6 carbon atoms and 1–4 substituents independently selected from —F, —Cl, —Br, and —I;

Halogenated heterocycloalkyl is a cyclic ring moiety having from 4–7 atoms with 1–2 atoms within the ring selected from N, O, and S, and 1–4 substituents independently selected from —F, —Cl, —Br, and —I;

$R_3$ is H, halogen, $C_1$–$C_6$ alkyl, substituted alkyl, or aryl;

$R_4$ is H, $C_1$–$C_6$ alkyl, substituted alkyl, or aryl;

Provided that $R_3$ and $R_4$ may not both be H;

$R_5$ is hydrogen, halogen, $C_1$–$C_4$ alkyl, substituted alkyl, —$OC_1$–$C_6$ alkyl, substituted —$OC_1$–$C_6$ alkyl, CN, $NO_2$, OH, —$N_3$, $NR_1R_2$, —C(O)$NR_1R_2$, —C(S)$NR_1R_2$, —O-aryl, or aryl;

Substituted —$OC_1$–$C_6$ alkyl is an —$OC_1$–$C_6$ alkyl moiety in which the alkyl is a substituted alkyl;

Aryl is phenyl, naphthyl, hetereoaromatic, substituted phenyl, substituted naphthyl, or substituted heteroaromatic;

Heteroaromatic is a 5, 6, or 10 member heteroaromatic ring containing 1 to 3 hetero atoms selected from N, O, and S;

Substituted phenyl is a phenyl group having 1 to 3 substituents selected from halogen, $C_1$–$C_4$ alkyl, substituted $C_1$–$C_6$ alkyl, —O—$C_1$–$C_4$ alkyl, substituted —O—$C_1$–$C_4$ alkyl, CN, $NO_2$, OH, —$N_3$, $NR_1R_2$, —C(O)$NR_1R_2$, and —C(S) $NR_1R_2$;

Substituted naphthyl is a naphthyl group having 1 to 3 substituents selected from halogen, $C_1$–$C_4$ alkyl, substituted $C_1$–$C_6$ alkyl, —$OC_1$–$C_6$ alkyl, substituted —O—$C_1$–$C_4$ alkyl, CN, $NO_2$, OH, —$N_3$, $NR_1R_2$, —C(O)$NR_1R_2$, and —C(S)$NR_1R_2$;

Substituted heteroaromatic is a heteroaromatic ring 1 to 3 substituents selected from halogen, $C_1$–$C_4$ alkyl, substituted $C_1$–$C_6$ alkyl, —$OC_1$–$C_6$ alkyl, substituted —O—$C_1$–$C_4$ alkyl, CN, $NO_2$, OH, —$N_3$, $NR_1R_2$, —C(O)$NR_1R_2$, and —C(S)$NR_1R_2$, tetrazoyl, triazoyl, amidinyl, guanidinyl, thioguanidinyl, cyanoguanidinyl;

and pharmaceutically acceptable salts thereof are useful for treating anxiety, depression, schizophrenia, stress-related disorders such as irritable bowel syndrome, panic, a phobia, obsessive compulsive disorder, obesity, post-traumatic stress syndrome, epilepsy, and other central nervous system (CNS) disorders in humans and animals, including cognitive disorders such as mild cognitive impairment, Alzhiemer's disease, and attention deficit disorder with or without hyperactivity.

Embodiments of the invention may include one or more of the following. $R_1$ is H, $C_1$–$C_6$ alkyl, or aryl. $R_2$ is H, $C_1$–$C_6$ alkyl, or aryl. $R_3$ is H, halogen, $C_1$–$C_6$ alkyl, or aryl. $R_4$ is H, $C_1$–$C_6$ alkyl, or aryl. $R_5$ is H. $R_3$ is H or $C_1$–$C_6$ alkyl. $R_4$ is H or $C_1$–$C_6$ alkyl. Aryl is phenyl or substituted phenyl. Substituted phenyl where the phenyl moiety is substituted with 1–3 substituents selected from H, halogen, $C_1$–$C_4$ alkyl, —O—$C_1$–$C_4$ alkyl, and $CF_3$. $R_1$ and $R_2$ are independently H or $C_1$–$C_6$ alkyl. Aryl is naphthyl or substituted naphthyl. Aryl is heteroaromatic or substituted heteroaromatic. $X_1$ and $X_2$ together form a bond between the C2 carbon and the C3 carbon of the indole-ring.

In another aspect, the invention features a compound or pharmaceutically acceptable salts thereof selected from the group consisting of:
2-[1-methyl-5-(phenylsulfonyl)-1H-indol-3-yl]ethanamine;
2-[2-methyl-5-(phenylsulfonyl)-1H-indol-3-yl]ethanamine;
N-methyl-2-[2-methyl-5-(phenylsulfonyl)-1H-indol-3-yl]ethanamine;
2-[1,2-dimethyl-5-(phenylsulfonyl)-1H-indol-3-yl]ethanamine;
2-[1,2-dimethyl-5-(phenylsulfonyl)-1H-indol-3-yl]-N-methylethanamine;
2-[1,2-dimethyl-5-(phenylsulfonyl)-1H-indol-3-yl]-N,N-dimethylethanamine;
2-{1-methyl-5-[(4-methylphenyl)sulfonyl]-1H-indol-3-yl}ethanamine;
N-methyl-2-{1-methyl-5-[(4-methylphenyl)sulfonyl]-1H-indol-3-yl}ethanamine;
2-{2-methyl-5-[(4-methylphenyl)sulfonyl]-1H-indol-3-yl}ethanamine;
2-{1,2-dimethyl-5-[(4-methylphenyl)sulfonyl]-1H-indol-3-yl}ethanamine;
2-{1,2-dimethyl-5-[(4-methylphenyl)sulfonyl]-1H-indol-3-yl}-N-methylethanamine;
2-(2-methyl-5-{[4-(trifluoromethyl)phenyl]sulfonyl}-1H-indol-3-yl)ethanamine;
2-(1,2-dimethyl-5-{[4-(trifluoromethyl)phenyl]sulfonyl}-1H-indol-3-yl)ethanamine;
2-(1,2-dimethyl-5-{[4-(trifluoromethyl)phenyl]sulfonyl}-1H-indol-3-yl)-N-methylethanamine;
2-{5-[(3-methoxyphenyl)sulfonyl]-2-methyl-1H-indol-3-yl}ethanamine;
2-{5-[(3-methoxyphenyl)sulfonyl]-1,2-dimethyl-1H-indol-3-yl}ethanamine;
2-{5-[(3-methoxyphenyl)sulfonyl]-1,2-dimethyl-1H-indol-3-yl}-N-methylethanamine;
2-{5-[(3,5-difluorophenyl)sulfonyl]-2-methyl-1H-indol-3-yl}ethanamine;
2-{5-[(3,5-difluorophenyl)sulfonyl]-1,2-dimethyl-1H-indol-3-yl}ethanamine;
2-{5-[(3,5-difluorophenyl)sulfonyl]-1,2-dimethyl-1H-indol-3-yl}-N-methylethanamine;
2-[2-methyl-5-(1-naphthylsulfonyl)-1H-indol-3-yl]ethanamine, and
2-[1,2-dimethyl-5-(1-naphthylsulfonyl)-1H-indol-3-yl]ethanamine.

In yet another aspect, the invention features a compound or pharmaceutically acceptable salts thereof, selected from the group consisting of: 2-[1-methyl-5-(phenylsulfonyl)-1H-indol-3-yl]ethanamine, 2-[1,2-dimethyl-5-(phenylsulfonyl)-1H-indol-3-yl]ethanamine, 2-{5-[(3-methoxyphenyl)sulfonyl]-1,2-dimethyl-1H-indol-3-yl}ethanamine, 2-{5-[(3,5-difluorophenyl)sulfonyl]-1,2-dimethyl-1H-indol-3-yl}-N-methylethanamine, 2-[2-methyl-5-(1-naphthylsulfonyl)-1H-indol-3-yl]ethanamine, 2-[1,2-dimethyl-5-(1-naphthylsulfonyl)-1H-indol-3-yl]ethanamine, and 2-[1,2-dimethyl-5-(1-naphthylsulfonyl)-1H-indol-3-yl]-N-methylethanamine.

The compounds of formula I also can include isotopic labels. For example the compounds 2-[1-methyl-5-(phenylsulfonyl)-1H-indol-3-yl]ethanamine; 2-[1,2-dimethyl-5-(phenylsulfonyl)-1H-indol-3-yl]-N-methylethanamine; 2-[1,2-dimethyl-5-(phenylsulfonyl)-1H-indol-3-yl]ethanamine; 2-{5-[(3,5-difluorophenyl)sulfonyl]-1,2-dimethyl-1H-indol-3-yl}ethanamine; 2-{5-[(3,5-difluorophenyl)sulfonyl]-1,2-dimethyl-1H-indol-3-yl}-N-methylethanamine; 2-[2-methyl-5-(1-naphthylsulfonyl)-1H-indol-3-yl]ethanamine; and pharmaceutically acceptable salts thereof may contain an isotopic label such as at least one atom selected from Carbon-11, Nitrogen-13, Oxygen-15, and Fluorine-18. Isotopically labeled compounds may be used in positron emission tomography.

In other embodiments, compounds 2-{5-[(3,5-difluorophenyl)sulfonyl]-1,2-dimethyl-1H-indol-3-yl}ethanamine; 2-{5-[(3,5-difluorophenyl)sulfonyl]-1,2-dimethyl-1H-indol-3-yl}-N-methylethanamine, and pharmaceutically acceptable salts thereof, each containing at least one $^{19}F$ atom may be used in nuclear magnetic resonance imaging.

The compounds of the present invention are useful in the treatment of $5\text{-HT}_6$ implicated diseases or conditions, such as anxiety, depression, schizophrenia, stress-related disorders such as irritable bowel syndrome, panic, a phobia, obsessive compulsive disorder, obesity, post-traumatic stress syndrome, epilepsy, and other central nervous system (CNS) disorders in humans and animals. Methods for treating a disease or condition in a mammal, in which $5\text{-HT}_6$ receptor is implicated, includes administering to a mammal, rectally, topically, orally, sublingually, or parenterally, from about 0.001 to about 100 mg/kg, e.g., from about 0.1 to about 50 mg/kg, of body weight of said mammal per day of compound(s) of Formula I.

The 5-arylsulfonyl indoles (I) of the present invention interact with serotonin receptors, such as $5\text{-HT}_6$ receptors, and are useful in the treatment of anxiety, depression, schizophrenia, Alzheimer's disease, stress-related disorders such as irritable bowel syndrome, panic, a phobia, obsessive compulsive disorder, obesity, post-traumatic stress syndrome, epilepsy, and other CNS disorders. It is preferred that the 5-arylsulfonyl indole (I) be used to treat anxiety or depression.

To treat anxiety, depression, or other CNS diseases, the 5-arylsulfonyl indoles (I) are administered orally, sublingually, transdermally or parenterally to provide a dosage of about 0.1 to about 50 mg/kg/day. It is preferred that the dosage range be from about 0.1 to about 10 mg/kg/day. The 5-arylsulfonyl indoles (I) can be administered in divided doses either two, three or four times daily. For parenteral administration, a saline solution, dextrose solution, or water may be used as a suitable carrier. Formulations for parenteral administration may be in the form of aqueous or non-aqueous isotonic sterile injection solutions or suspensions. These solutions and suspensions may be prepared from sterile powders or granules having one or more of the carriers or diluents mentioned for use in the formulations for oral administration. The compounds may be dissolved in water, polyethylene glycol, propylene glycol, ethanol, corn oil, cottonseed oil, peanut oil, sesame oil, benzyl alcohol, sodium chloride, and/or various buffers. Other adjuvants and modes of administration are well and widely known in the pharmaceutical art. It is preferred that the 5-arylsulfonyl indoles (I) be administered orally.

The exact dosage and frequency of administration depends on the particular 5-arylsulfonyl indole(s) used, the particular disease being treated, the severity of the disease being treated, the age, weight, general physical condition of the particular patient, other medication the individual may be taking as is well known to those skilled in the art and can be more accurately determined by measuring the blood level or concentration of the 5-arylsulfonyl indole (I) in the patient's blood and/or the patient's response to the particular condition being treated.

The 5-arylsulfonyl indole (I) compounds of the present invention may be incorporated into pharmaceutical compositions for treating different CNS diseases, such as anxiety or depression. The pharmaceutical compositions may include one or more 5-arylsulfonyl indole (I) compounds. The compositions also may contain well known carriers and excipients in addition to a therapeutically effective amount of compounds of Formula I. The term "carrier" material or "excipient" herein means any substance, not itself a therapeutic agent, used as a carrier and/or diluent and/or adjuvant, or vehicle for delivery of a therapeutic agent to a subject or added to a pharmaceutical composition to improve its handling or storage properties or to permit or facilitate formation of a dose unit of the composition into a discrete article such as a capsule or tablet suitable for oral administration. Excipients can include, by way of illustration and not limitation, diluents, disintegrants, binding agents, adhesives, wetting agents, polymers, lubricants, glidants, substances added to mask or counteract a disagreeable taste or odor, flavors, dyes, fragrances, and substances added to improve appearance of the composition. Acceptable excipients include lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinyl-pyrrolidone, and/or polyvinyl alcohol, and then tableted or encapsulated for convenient administration. Such capsules or tablets may contain a controlled-release formulation as may be provided in a dispersion of active compound in hydroxypropyl-methyl cellulose, or other methods known to those skilled in the art. For oral administration, the pharmaceutical composition may be in the form of, for example, a tablet, capsule, suspension or liquid. If desired, other active ingredients may be included in the composition.

In addition to the oral dosing, noted above, the compositions of the present invention may be administered by any suitable route, in the form of a pharmaceutical composition adapted to such a route, and in a dose effective for the treatment intended. The compositions may, for example, be administered parenterally, e.g., intravascularly, intraperitoneally, subcutaneously, or intramuscularly. For parenteral administration, saline solution, dextrose solution, or water may be used as a suitable carrier. Formulations for parenteral administration may be in the form of aqueous or non-aqueous isotonic sterile injection solutions or suspensions. These solutions and suspensions may be prepared from sterile powders or granules having one or more of the carriers or diluents mentioned for use in the formulations for oral administration. The compounds may be dissolved in water, polyethylene glycol, propylene glycol, ethanol, corn oil, cottonseed oil, peanut oil, sesame oil, benzyl alcohol, sodium chloride, and/or various buffers. Other adjuvants and modes of administration are well and widely known in the pharmaceutical art.

The invention also includes isotopically-labeled compounds, which are identical to those recited in Formula 1, but for the fact that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorous, fluorine, iodine, and chlorine, such as $^3H$, $^{11}C$, $^{14}C$, $^{13}N$, $^{15}O$, $^{18}F$, $^{99m}Tc$, $^{123}I$, and $^{125}$. Compounds of the present invention and pharmaceutically acceptable salts and prodrugs of said compounds that contain the aforementioned isotopes and/or other isotopes of other atoms are within the scope of the invention.

Isotopically-labeled compounds of the present invention are useful in drug and/or substrate tissue distribution and target occupancy assays. For example, isotopically labeled compounds are particularly useful in SPECT (single photon emission computed tomography) and in PET (positron emission tomography).

Single-photon emission computed tomography (SPECT), acquires information on the concentration of isotopically labeled compounds introduced to a mammal's body. SPECT dates from the early 1960's, when the idea of emission traverse section tomography was introduced by D. E. Kuhl and R. Q. Edwards prior to either PET, x-ray CT, or MRI. In general, SPECT requires isotopes that decay by electron capture and/or gamma emission. Example of viable SPECT isotopes include, but are not limited to, 123-iodine ($^{123}I$) and 99m-technetium ($^{99m}Tc$). Subjects are injected with a radioactively labeled agent, typically at tracer doses. The nuclear decay resulting in the emission of a single gamma ray which passes through the tissue and is measured externally with a SPECT camera. The uptake of radioactivity reconstructed by computers as a tomogram shows tissue distribution in cross-sectional images.

Positron emission tomography (PET) is a technique for measuring the concentrations of positron-emitting isotopes within the tissues. Like SPECT, these measurements are, typically, made using PET cameras outside of the living subjects. PET can be broken down into several steps including, but not limited to, synthesizing a compound to include a positron-emitting isotope; administering the isotopically labeled compound to a mammal; and imaging the distribution of the positron activity as a function of time by emission tomography. PET is described, for example, by Alavi, et al. in Positron Emission Tomography, published by Alan R. Liss, Inc. in 1985.

Positron-emitting isotopes used in PET include, but are not limited to, Carbon-11, Nitrogen-13, Oxygen-15, and Fluorine-18. In general, positron-emitting isotopes should have short half-lives to help minimize the long-term radiation exposure that a patient receives from high dosages required during PET imaging.

In certain instances, PET imaging can be used to measure the binding kinetics of compounds of this invention with 5-HT$_6$ serotonin receptors. For example, administering an isotopically labeled compound of the invention that penetrates into the body and binds to a 5-HT$_6$ serotonin receptor creates a baseline PET signal which can be monitored while administering a second, different, non-isotopically labeled compound. The baseline PET signal will decrease as the non-isotopically labeled compound competes for the binding to the 5-HT$_6$ serotonin receptor.

In general, compounds of formula I that are useful in performing PET or SPECT are those which penetrate the blood-brain barrier, exhibit high selectivity and modest affinity to 5-HT$_6$ serotonin receptors, and are eventually metabolized. Compounds that are non-selective or those that exhibit excessive or small affinity for 5-HT$_6$ serotonin receptors are, generally, not useful in studying brain receptor binding kinetics with respect to 5-HT$_6$ serotonin receptors. Compounds that are not metabolized may harm the patient. Preferred compounds for isotopic labeling and use in performing PET or SPECT include 2-[1-methyl-5-(phenylsulfonyl)-1H-indol-3-yl]ethanamine; 2-[1,2-dimethyl-5-(phenylsulfonyl)-1H-indol-3-yl]-N-methylethanamine; 2-[1,2-dimethyl-5-(phenylsulfonyl)-1H-indol-3-yl]ethanamine; 2-{5-[(3,5-difluorophenyl)sulfonyl]-1,2-dimethyl-1H-indol-3-yl}ethanamine; 2-{5-[(3,5-difluorophenyl)sulfonyl]-1,2-dimethyl-1H-indol-3- yl}-N-methylethanamine; 2-[2-methyl-5-(1-naphthylsulfonyl)-1H-indol-3-yl]ethanamine; and pharmaceutically acceptable salts thereof.

In other embodiments, nuclear magnetic resonance spectroscopy (MRS) imaging can be used to detect the overall concentration of a compound or fragment thereof containing nuclei with a specific spin. In general, the isotopes useful in NMR imaging include, but are not limited to, hydrogen-1, carbon-13, phosphorus-31, and fluorine-19. For instance, compounds 2-{5-[(3,5-difluorophenyl)sulfonyl]-1,2-dimethyl-1H-indol-3-yl}ethanamine; 2-{5-[(3,5-difluorophenyl)sulfonyl]-1,2-dimethyl-1H-indol-3-yl}-N-methylethanamine; and pharmaceutically acceptable salts thereof, when containing $^{19}F$ are useful in conducting NMR imaging.

Further, substitution with heavier isotopes such as deuterium, i.e., $^2H$, can afford certain therapeutic advantages resulting from greater metabolic stability, for example increased in vivo half-life or reduced dosage requirements and, hence, maybe preferred in some circumstances. Isotopically labeled compounds of Formula I of this invention can generally be prepared by carrying out the synthetic procedures described above by substituting an isotopically labeled reagent for a non-isotopically labeled reagent.

Definitions and Conventions

The definitions and explanations below are for the terms as used throughout this entire document including both the specification and the claims.

I. Conventions for Formulas and Definitions of Variables

The chemical formulas representing various compounds or molecular fragments in the specification and claims may contain variable substituents in addition to expressly defined structural features. These variable substituents are identified by a letter or a letter followed by a numerical subscript, for example, "$Z_1$" or "$R_i$" where "i" is an integer. These variable substituents are either monovalent or bivalent, that is, they represent a group attached to the formula by one or two chemical bonds. For example, a group $Z_1$ would represent a bivalent variable if attached to the formula $CH_3-C(=Z_1)$H. Groups $R_i$ and $R_j$ would represent monovalent variable substituents if attached to the formula $CH_3-CH_2-C(R_i)$ ($R_j$)—H. When chemical formulas are drawn in a linear fashion, such as those above, variable substituents contained in parentheses are bonded to the atom immediately to the left of the variable substituent enclosed in parenthesis. When two or more consecutive variable substituents are enclosed in parentheses, each of the consecutive variable substituents is bonded to the immediately preceding atom to the left, which is not enclosed in parentheses. Thus, in the formula above, both $R_i$ and $R_j$ are bonded to the preceing carbon atom. Also, for any molecule with an established system of carbon atom numbering, such as steroids, these carbon atoms are designated as $C_i$, where "i" is the integer corresponding to the carbon atom number. For example, $C_6$ represents the 6 position or carbon atom number in the steroid nucleus as traditionally designated by those skilled in the art of steroid chemistry. Likewise the term "$R_6$" represents a variable substituent (either monovalent or bivalent) at the $C_6$ position.

Chemical formulas or portions thereof drawn in a linear fashion represent atoms in a linear chain. The symbol "–" in general represents a bond between two atoms in the chain. Thus $CH_3-O-CH_2-CH(R_i)-CH_3$ represents a 2-substituted-1-methoxypropane compound. In a similar fashion, the symbol "=" represents a double bond, e.g., $CH_2=C(R_i)-O-CH_3$.

The carbon atom content of variable substituents is indicated in one of two ways. The first method uses a prefix to the entire name of the variable such as "$C_1-C_4$", where both "1" and "4" are integers representing the minimum and maximum number of carbon atoms in the variable. The prefix is separated from the variable by a space. For example, "$C_1-C_4$ alkyl" represents alkyl of 1 through 4 carbon atoms, (including isomeric forms thereof unless an express indication to the contrary is given). Whenever this single prefix is given, the prefix indicates the entire carbon atom content of the variable being defined. Thus $C_2-C_4$ alkoxycarbonyl describes a group $CH_3-(CH_2)_n-O-CO-$ where n is zero, one or two. By the second method the carbon atom content of only each portion of the definition is indicated separately by enclosing the "$C_i-C_j$" designation in parentheses and placing it immediately (no intervening space) before the portion of the definition being defined. By this optional convention ($C_1-C_3$)alkoxycarbonyl has the same meaning as $C_2-C_4$ alkoxycarbonyl because the "$C_1-C_3$" refers only to the carbon atom content of the alkoxy group. Similarly while both $C_2-C_6$ alkoxyalkyl and ($C_1-C_3$) alkoxy($C_1-C_3$)alkyl define alkoxyalkyl groups containing from 2 to 6 carbon atoms, the two definitions differ since the former definition allows either the alkoxy or alkyl portion alone to contain 4 or 5 carbon atoms while the latter definition limits either of these groups to 3 carbon atoms.

II. Definitions

Alkyl is both straight- and branched-chain moieties having from 1–6 carbon atoms. For example, $C_{1-6}$ alkyl includes methyl, ethyl, propyl, isopropyl, butyl, iso-butyl, sec-butyl, pentyl, 3-pentyl, hexyl, and isomeric forms thereof.

Ar refers to Aryl.

BOC refers to —C(O)O-t-butyl.

All temperatures are in degrees Centigrade.

HPLC refers to high pressure liquid chromatography.

DMSO refers to dimethylsulfoxide.

DMF refers to N,N-dimethylformamide.

Saline refers to an aqueous saturated sodium chloride solution.

Chromatography (column and flash chromatography) refers to purification/separation of compounds expressed as (support, eluent). It is understood that the appropriate fractions are pooled and concentrated to give the desired compound(s).

IR refers to infrared spectroscopy.

NMR refers to nuclear (proton) magnetic resonance spectroscopy, chemical shifts are reported in ppm (d) downfield from tetramethylsilane.

MS refers to mass spectrometry expressed as m/e, m/z or mass/charge unit. [M+H]$^+$ refers to the positive ion of a parent plus a hydrogen atom. EI refers to electron impact. CI refers to chemical ionization. FAB refers to fast atom bombardment.

HRMS refers to high resolution mass spectrometry.

Pharmaceutically acceptable refers to those properties and/or substances which are acceptable to the patient from a pharmacological/toxicological point of view and to the manufacturing pharmaceutical chemist from a physical/chemical point of view regarding composition, formulation, stability, patient acceptance and bioavailability.

When solvent pairs are used, the ratios of solvents used are volume/volume (v/v).

When the solubility of a solid in a solvent is used the ratio of the solid to the solvent is weight/volume (wt/v).

Compounds of the present invention may be in the form of pharmaceutically acceptable salts. The term "pharmaceutically acceptable salts" refers to salts prepared from pharmaceutically acceptable non-toxic bases including inorganic bases and organic bases, and salts prepared from inorganic acids, and organic acids. Salts derived from inorganic bases include aluminum, ammonium, calcium, ferric, ferrous, lithium, magnesium, potassium, sodium, zinc, and the like. Salts derived from pharmaceutically acceptable organic non-toxic bases include salts of primary, secondary, and tertiary amines, substituted amines including naturally occurring substituted amines, cyclic amines, such as arginine, betaine, caffeine, choline, N,N-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, and the like. Salts derived from inorganic acids include salts of hydrochloric acid, hydrobromic acid, hydroiodic acid, sulfuric acid, phosphoric acid, phosphorous acid and the like. Salts derived from pharmaceutically acceptable organic non-toxic acids include salts of $C_{1-6}$ alkyl carboxylic acids, di-carboxylic acids, and tri-carboxylic acids such as acetic acid, propionic acid, fumaric acid, succinic acid, tartaric acid, maleic acid, adipic acid, and citric acid, and aryl and alkyl sulfonic acids such as toluene sulfonic acids and the like.

By the term "effective amount" of a compound as provided herein is meant a nontoxic but sufficient amount of the compound(s) to provide the desired effect. As pointed out below, the exact amount required will vary from subject to subject, depending on the species, age, and general condition of the subject, the severity of the disease that is being treated, the particular compound(s) used, the mode of administration, and the like. Thus, it is not possible to specify an exact "effective amount." However, an appropriate effective amount may be determined by one of ordinary skill in the art using only routine experimentation.

Preparation of 5-Arylsulfonyl Indoles

The 5-arylsulfonyl indoles of the present invention may be prepared using the following reaction schemes:

Arylsulphonylphenylhydrazines can be prepared by the reactions outlined in Chart 1. The appropriately substituted thiols (1) are either known to those skilled in the art or can be readily prepared from known starting materials by means well known to those skilled in the art. Thiol (1) is coupled with the appropriately substituted 4-chloro-1-nitrobenzene (2) by known means to produce the thioether (3). There can be either one or two $R^5$ groups. If $R^5$ is other than —H, it should be part of the 4-chloro-1-nitrobenzene (2) so that it will become part of the unsubstituted arylsulfone (8) when it is formed. It is most difficult to add the $R^5$ substitutent (other than —H) to the unsubstituted arylsulfone (8) once it is formed. Therefore, the $R^5$ group should be part of the appropriately substituted 4-chloro-1-nitrobenzene (2) when it is reacted with the thiol (1). $R^5$ includes —H, —F and —Cl; it is preferred that $R^5$ is —H. The thioether (3) is then oxidized with oxone followed by hydrogenation with rhodium on carbon (5%), all of which is known to those skilled in the art, to produce the amine (5). The amine (5) is then diazotized by (sodium) nitrite and (hydrochloric) acid followed by reduction with tin chloride to give the corresponding hydrazine (6).

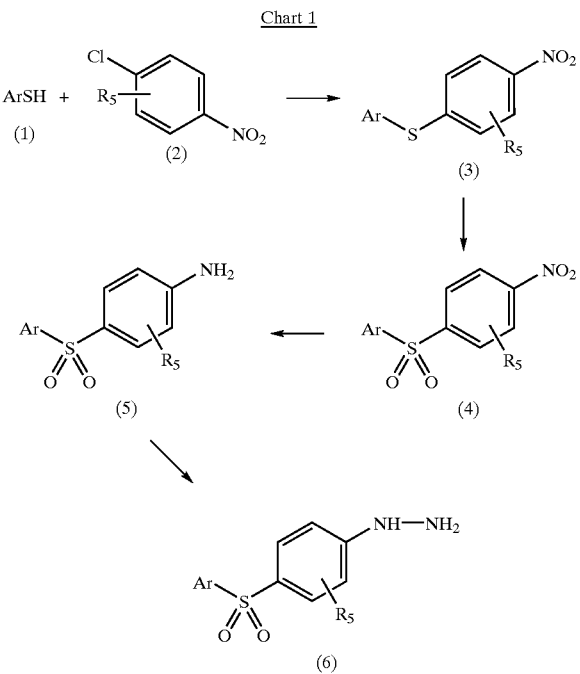

Chart 1

Compounds of formula I can be prepared by the reactions outlined in Chart 2. Grandberg reaction using hydrazine (6) with γ-chloroketones (7) gives the formation of the indole (8). The amino group is protected with Boc to give compound (9), in which the indole nitrogen is alkylated with cesium carbonate in acetone and alkylating reagents (e.g. $Me_2SO_4$, alkyl halides). Compound (10) is further alkylated with sodium hydride and alkyl halides to generate compound (11). After deprotection, compound (12) is produced. Under reductive amination conditions with sodium cyanoborohydride in acetonitrile in the presence of aldehydes, compound (12) is converted to compound (13). The γ-chloroketones (7) are commercially available or can be made by procedures well known in the art. The procedures and conditions for the Grandberg, protection, deprotection, alkylation and reductive amination steps of Chart 2 are well known to those skilled in the art.

Chart 2
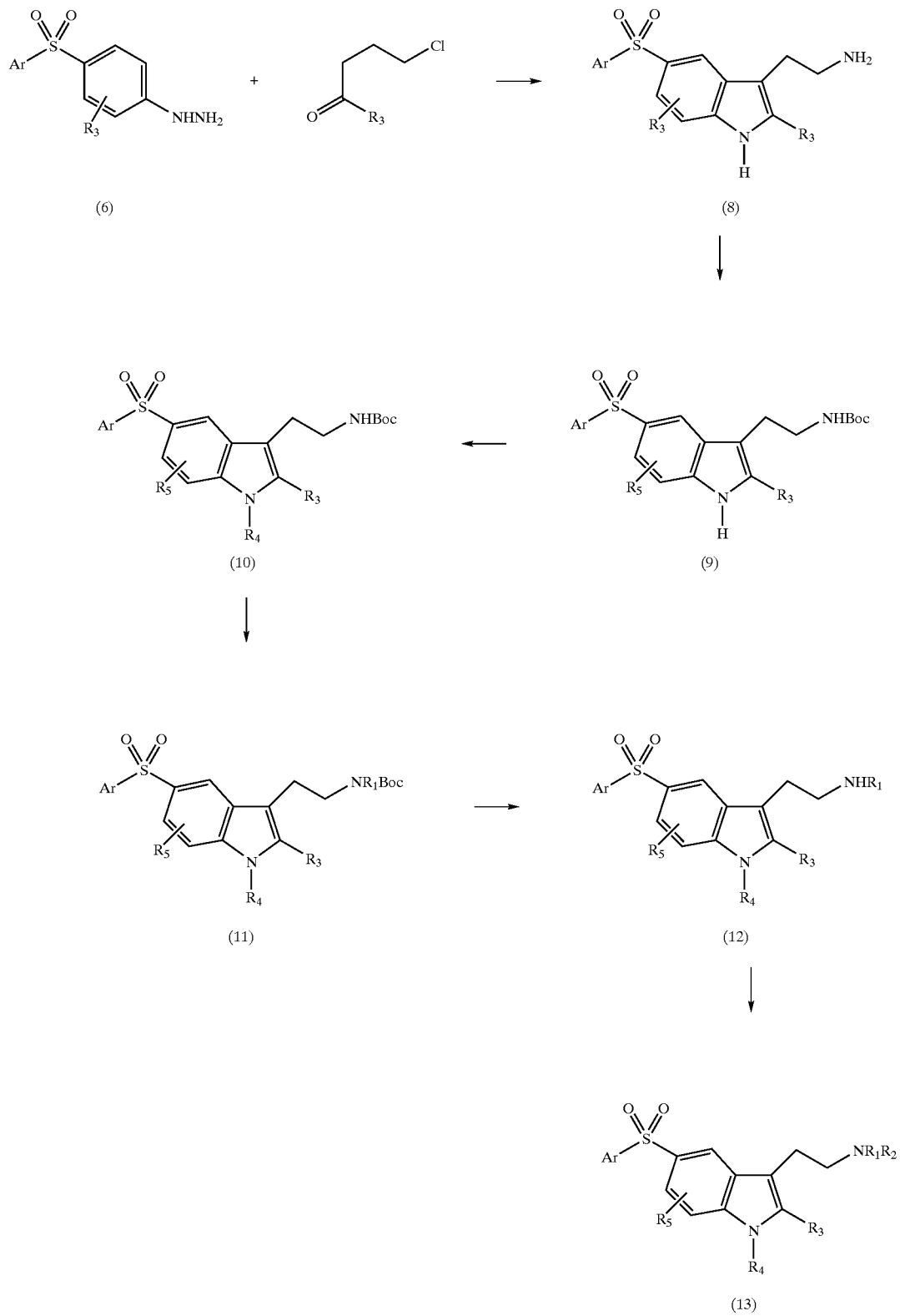

Compounds of formula I can also be prepared by the reactions outlined in Chart 3. The Boc protected compound (9) is reduced with LiAlH₄ to lead to the formation of the corresponding methyl compound (14).

Chart 3

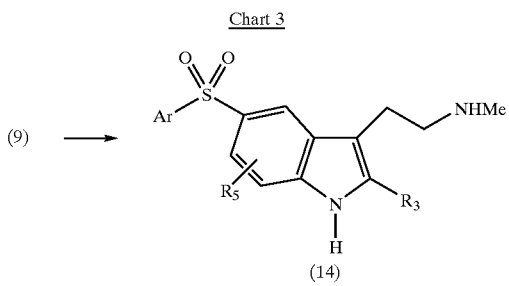

Compounds of formula I can also be prepared by the reactions outlined in Chart 4. The Boc protected compound (10) is treated with acids (e.g. HCl) to lead to the formation of the amino compound (15).

Chart 4

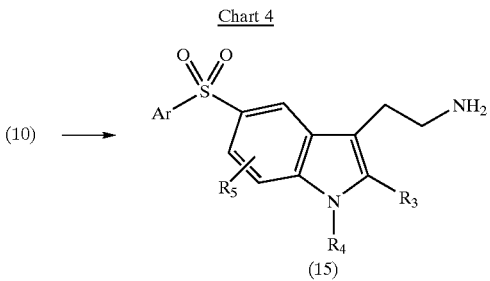

Compounds of formula I can also be prepared by the reactions outlined in Chart 5. The indole compound (13) is treated with a reducing reagent such as sodium cyanoborohydride in an acid media such as trifluoroacetic acid or acetic acid to lead to the formation of the indoline compound (16).

Chart 5

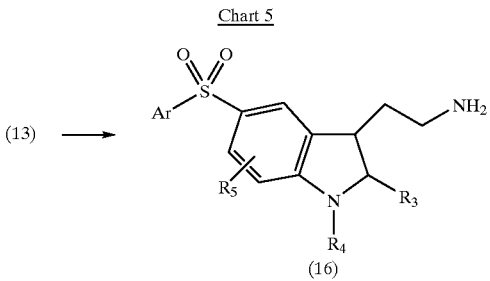

EXAMPLES

Without further elaboration, it is believed that one skilled in the art can, using the preceding description, practice the present invention to its fullest extent. The following detailed examples describe how to prepare the various compounds and/or perform the various processes of the invention and are to be construed as merely illustrative, and not limitations of the preceding disclosure in any way whatsoever. Those skilled in the art will promptly recognize appropriate variations from the procedures both as to reactants and as to reaction conditions and techniques.

Preparation 1: Preparation of 4-[(4'-methylphenyl)sulfonyl]-1-phenylhydrazine

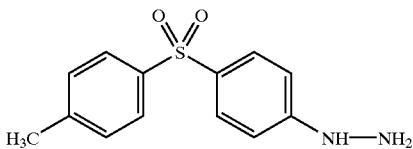

Step 1: Preparation of 4-[(4'-methylphenyl)thio]-1-nitrobenzene.

A mixture of 4-methylbenzenethiol (40.0 g, 0.322 mol), 1-chloro-4-nitrobenzene (55.5 g, 0.352 mol) and K₂CO₃ (89.0 g, 0.644 mol) in acetonitrile (1.3 L) was stirred at room temperature under nitrogen for 20 h. The mixture was diluted with H₂O (2.0 L) and extracted with CH₂Cl₂ (3×1.0 L). The combined extracts were dried over Na₂SO₄, concentrated in vacuo, and the crude product was recrystallized from (2.5:7) EtOAc/hexane (950 mL) to give 52.0 g (66%) of the title compound as a colorless solid. ¹H NMR (300 MHz, CDCl₃) δ 2.41 (s, 3H), 7.14 (d, J=9.0 Hz, 2H), 7.27 (d, J=8.4 Hz, 2H), 7.44 (d, J=8.4 Hz, 2H), 8.04 (d, J=9.0 Hz, 2H).

Step 2: Preparation 4-[(4'-methylphenyl)sulfonyl]-1-nitrobenzene.

To a 0° C. solution of 4-[(4'-methylphenyl)thio]-1-nitrobenzene (50.0 g, 0.204 mol) in (1:1) THF/CH₃OH (3.0 L) was added a solution of oxone (280.0 g, 0.440 mol) in H₂O (1.5 L) over 30 min. The reaction was stirred for 16 h while allowing the cooling bath to expire. The solution was concentrated to ~1/3 the original volume and filtered. The solids were washed with H₂O (300 mL) and Et₂O (100 mL) then dried under vacuum to give the crude product, which was recrystallized from (1:4) EtOAc/hexane (1.0 L) to afford 43.0 g (77%) of the title compound as a colorless solid. ¹H NMR (300 MHz, CDCl₃) δ 2.43 (s, 3H), 7.37 (d, J=8.1 Hz, 2H), 7.87 (d, J=8.1 Hz, 2H), 8.13 (d, J=9.0 Hz, 2H), 8.35 (d, J=9.0 Hz, 2H).

Step 3: Preparation of 4-[(4'-methylphenyl)sulfonyl]-aniline.

To a solution of 4-[(4'-methylphenyl)sulfonyl]-1-nitrobenzene, (30.0 g, 0.1 mol) in CH₃OH (1.2 L) in a Paar bottle was added with 5%$_{wt}$ Rh on C (2.8 g) and the resulting mixture was alternatively evacuated and purged with H₂ (×5), then shaken under H₂ (55 psi) for 48 h. The reaction mixture was filtered through a bed of celite and the solids were rinsed with CH₂Cl₂ (1.0 L) and CH₃OH (1.0 L). The combined filtrates were concentrated in vacuo to afford 24.54 g (92%) of colorless solid, which was used without further purification. ¹H NMR (CDCl₃) δ 2.37 (s, 3H), 4.20 (br, 2H), 6.65 (d, J=9.0 Hz, 2H), 7.26 (d, J=7.2 Hz, 2H), 7.69 (d, J=8.7 Hz, 2H), 7.78 (d, J=8.4 Hz, 2H).

Step 4: Preparation of 4-[(4'-methylphenyl)sulfonyl]-1-phenylhydrazine.

To a 0° C. solution of 4-[(4'-methylphenyl)sulfonyl]aniline (23.0 g, 93.0 mmol) in concentrated HCl (250 mL) was added a solution of NaNO₂ (7.2 g, 0.104 mol) in H₂O (113 mL) dropwise over 15 min. The resulting heterogeneous mixture was stirred for 30 min at 0° C. then a solution of SnCl₂ (42.9 g, 0.226 mol) in concentrated HCl (114 mL) was dropwise added over 10 min. The reaction mixture was stirred at 0° C. for 1 hr, then the cooling bath was removed and stirring was continued at room temperature for 1 h. The reaction mixture was filtered and the solids were suspended in H₂O (150 mL) and the suspension was made basic (pH>12) by addition of 50%$_{wt}$ NaOH. The mixture was filtered and the solid was dissolved in $CH_2Cl_2$ (600 mL) and washed with brine (200 mL). The organic layer was dried over anhydrous $Na_2SO_4$, filtered and concentrated in vacuo to provide the crude product, which was purified by recrystallizing from (1:5) $CH_2Cl_2$/hexane (950 mL) to afford 19.2 g (79%) of the title compound as a pale yellow solid: mp 158–160° C., in ~95% purity by $^1$H NMR. $^1$H NMR (300 MHz, DMSO-$d_6$) δ 2.33 (s, 3H), 4.24 (s, 2H), 6.83 (d, J=8.7 Hz, 2H), 7.36 (d, J=8.1 Hz, 2H), 7.60 (d, J=8.7 Hz, 2H), 7.73 (d, J=8.1 Hz, 2H), 7.76 (s, 1H); $^{13}$C (75 MHz, $d_6$-DMSO) δ 20.89, 110.16, 125.93, 126.47, 128.92, 129.79, 140.52, 142.89, 159.82. IR (ATR) 3335, 3285, 3135, 3090, 3064, 3033, 2979, 1585, 1511, 1347, 1287, 1141, 1101, 1072, 996 $cm^{-1}$; MS (ESI+); 263.0 [MH]$^+$.

Example 1

2-[1-methyl-5-(phenylsulfonyl)-1H-indol-3-yl]ethanamine hydrochloride

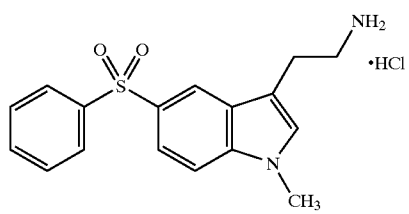

Step 1: Preparation of 2-[5-(phenylsulfonyl)-1H-indol-3-yl]ethanamine

A solution of 1-[4-(phenylsulfonyl)phenyl]hydrazine (3.73 g, 15.0 mmol) and 4-chlorobutanal (1.76 g, 16.5 mmol) in 9:1 methanol/water (15.0 mL) was heated to reflux for 4 days. The reaction mixture was concentrated in vacuo and the residue dissolved in MeOH and treated with activated carbon and filtered. The filtrate was concentrated in vacuo and the residue was subjected to column chromatography (silica gel, 2% MeOH/CHCl$_3$ with 1% Et$_3$N) to give 2.18 g (48%) of a light brown solid as the title compound: mp 188–192° C. (EtOAc/MeOH); $^1$H NMR (400 MHz, DMSO-$d_6$) δ 11.47 (s, 1H), 8.22 (s, 1H), 7.95–7.93 (m, 2H), 7.64–7.55 (m, 4H), 7.52 (d, J=8.6 Hz, 1H), 7.38 (s, 1H), 3.17 (br, 2H), 2.84 (s, 4H); $^{13}$C NMR (100 MHz, DMSO-$d_6$) δ 142.8, 138.2, 132.8, 130.4, 129.4, 126.7, 125.7, 119.6, 119.2, 114.3, 112.3, 42.3, 28.2; IR (diffuse reflectance) 3114, 3091, 3052, 301.5, 2942, 2919, 2861, 1447, 1293, 1154, 1138, 816, 724, 687, 646 $cm^{-1}$; HRMS (FAB) calcd for $C_{16}H_{16}N_2O_2S$+H 301.1010, found 301.1004; Anal. Calcd for $C_{16}H_{16}N_2O_2S$·0.5$H_2O$: C, 62.12; H, 5.54; N, 9.05. Found: C, 62.06; H, 5.54; N, 8.90.

Step 2: Preparation of tert-butyl 2-[5-(phenylsulfonyl)-1H-indol-3-yl]ethylcarbamate Di-tert-butyl dicarbonate (1.63 g, 7.48 mmol) was added to a solution of 2-[5-(phenylsulfonyl)-1H-indol-3-yl]ethanamine (2.01 g, 6.70 mmol) and triethylamine (0.81 g, 7.98 mmol) in $CH_2Cl_2$ (30.0 mL). The reaction was stirred at room temperature for 5 hours then washed with 2N HCl, saturated $NaHCO_3$, brine, dried over $MgSO_4$, and concentrated in vacuo to give a brown foam. The foam was subjected to column chromatography (silica gel, 30% EtOAc/hexane) to give 0.58 g (22%) of a brown solid as the title compound: mp 174.1–176.3° C. (EtOAc/hexane); $^1$H NMR (400 MHz, DMSO-$d_6$) δ 11.43 (s, 1H), 8.22 (s, 1H), 7.93 (d, J=7.0 Hz, 2H), 7.64–7.55 (m, 4H), 7.52 (d, J=8.6 Hz, 1H), 7.37 (s, 1H), 6.93 (br, 1H), 3.22–3.18 (m, 2H), 2.87–2.84 (m, 2H), 1.38 (s, 9H); $^{13}$C NMR (100 MHz, DMSO-$d_6$) δ 155.5, 142.8, 138.1, 132.8, 130.4, 129.4, 126.7, 125.7, 119.6, 119.1, 113.9, 112.3, 77.4, 40.6, 28.2, 25.0; IR (diffuse reflectance) 3303, 1690, 1493, 1303, 1294, 1151, 1133, 1109, 812, 744, 715, 704, 691, 658, 639 $cm^{-1}$; HRMS (FAB) calcd for $C_{21}H_{24}N_2O_4S$+H 400.1457, found 400.1457. Anal. Calcd for $C_{21}H_{24}N_2O_4S$: C, 62.98; H, 6.04; N, 6.99. Found: C, 62.64; H, 6.12; N, 6.82.

Step 3: Preparation of tert-butyl 2-[1-methyl-5-(phenylsulfonyl)-1H-indol-3-yl]ethylcarbamate A solution of tert-butyl 2-[5-(phenylsulfonyl)-1H-indol-3-yl]ethylcarbamate (0.58 g, 1.46 mmol) in acetone (25.0 mL) was treated with $Cs_2CO_3$ (1.85 g, 5.68 mmol) and dimethyl sulfate (0.80 mL, 8.45 mmol). The reaction was stirred at room temperature for 3.5 hours then filtered. The filtrate was concentrated in vacuo and subjected to column chromatography (silica gel, 30% EtOAc/hexane) to give 0.41 g (68%) of a colorless solid as the title compound: mp 127.4–130.6° C.; $^1$H NMR (400 MHz, DMSO-d6) δ 8.22 (s, 1H), 7.93 (d, J=7.1 Hz, 1H), 7.65–7.55 (m, 5H), 7.35 (s, 1H), 6.93 (br, 1H), 3.77 (s, 3H), 3.20–3.18 (m, 2H), 2.86–2.82 (m, 2H), 1.37 (s, 9H); $^{13}$C NMR (100 MHz, DMSO-$d_6$) δ 155.5, 142.7, 138.3, 132.8, 130.5, 130.0, 129.4, 127.0, 126.7, 119.7, 119.3, 113.4, 110.7, 77.4, 41.1, 32.5, 28.1, 24.9; IR (diffuse reflectance) 1676, 1531, 1450, 1366, 1316, 1303, 1286, 1177, 1152, 1144, 1103, 797, 726, 692, 626 $cm^{-1}$; HRMS (FAB) calcd for $C_{22}H_{26}N_2O_4S$+H 414.1613, found 414.1619; Anal. Calcd for $C_{22}H_{26}N_2O_4S$: C, 63.74; H, 6.32; N, 6.76. Found: C, 63.78; H, 6.39; N, 6.80.

Step 4: Preparation of 2-[1-methyl-5-(phenylsulfonyl)-1H-indol-3-yl]ethanamine hydrochloride tert-Butyl 2-[1-methyl-5-(phenylsulfonyl)-1H-indol-3-yl]ethylcarbamate (0.048 g, 0.12 mmol) was dissolved in a 4.0 N HCl in dioxane (3.0 mL) and stirred at room temperature for 3.5 hours. The white precipitate was filtered and washed with ethyl acetate then recrystallized from MeOH/EtOAc to give 0.022 g (54%) of a white solid as the title compound: mp 285.3–292° C.; $^1$H NMR (400 MHz, DMSO-$d_6$) δ 8.29 (d, J=1.4 Hz, 1H), 8.02 (br, 3H), 7.96–7.94 (m, 2H), 7.69–7.56 (m, 5H), 7.47 (s, 1H), 3.79 (s, 3H), 3.06 (br, 4H); $^{13}$C NMR (100 MHz, DMSO-d6) δ 142.6, 138.4, 132.9, 130.9, 129.4, 126.8, 126.6, 119.9, 119.1, 111.0, 110.9, 32.6, 22.4; IR (diffuse reflectance) 3060, 2980, 2962, 2944, 2904, 1488, 1305, 1288, 1162, 1149, 799, 725, 691, 643, 619 $cm^{-1}$; HRMS (FAB) calcd for $C_{17}H_{18}N_2O_2S$+H 315.1167, found 315.1168; Anal. Calcd for $C_{17}H_{18}N_2O_2S$·HCl·0.5$H_2O$: C, 56.73; H, 5.60; N, 7.78. Found: C, 56.96; H, 5.60; N, 7.70.

Example 2

2-[2-methyl-5-(phenylsulfonyl)-1H-indol-3-yl]ethanamine hydrochloride

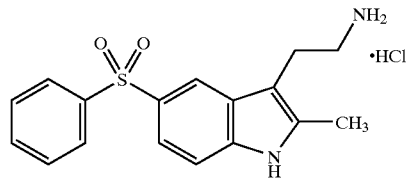

Following the general procedure of EXAMPLE 1 (Step 1) and making non-critical variations, the title compound was prepared by recrystalizing the crude product from MeOH/EtOAc to give a light brown solid (93%): mp>280° C.; $^1$H NMR (300 MHz, DMSO-$d_6$) δ 11.60 (s, 1H), 9.18 (s, 1H), 8.01 (br, 3H), 7.91 (d, J=8.1 Hz, 2H), 7.62–7.52 (m, 4H), 7.45 (d, J=1.4 Hz, 1H), 3.18–3.16 (m, 2H), 2.99–2.95 (m, 2H), 2.38 (s, 3H); IR (diffuse reflectance) 3279, 3206, 3089, 3059, 3007, 2984, 2916, 2884, 2839, 1298, 1284, 1156, 1118, 728, 689 cm$^{-1}$; HRMS (FAB) calcd for $C_{17}H_{18}N_2O_2S$+H 315.1167, found 315.1173; Anal. Calcd for $C_{17}H_{18}N_2O_2S \cdot HCl \cdot 0.25H_2O$: C, 57.45; H, 5.67; N, 7.88. Found: C, 57.57; H, 5.62; N, 7.81.

Example 3

N-methyl-2-[2-methyl-5-(phenylsulfonyl)-1H-indol-3-yl]ethanamine

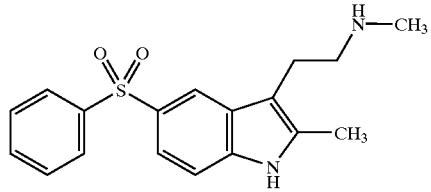

Step 1: Preparation of tert-butyl 2-[2-methyl-5-(phenylsulfonyl)-1H-indol-3-yl]ethylcarbamate Following the general procedure of EXAMPLE 1 (Step 2) and making non-critical variations, the title compound was prepared by recrystalizing the crude product from EtOAc as a colorless solid (79%): mp 210.2–213.0° C.; $^1$H NMR (400 MHz, Acetone-d$_6$) δ 10.40 (br, 1H), 7.99–7.96 (m, 2H), 7.59–7.52 (m, 4H), 7.44 (d, J=8.5 Hz, 1H), 6.05 (br, 1H), 3.31–3.26 (m, 2H), 2.96–2.92 (m, 2H), 2.43 (s, 3H), 1.46 (s, 9H); $^{13}$C NMR (100 MHz, Acetone-d$_6$) δ 156.7, 145.0, 138.7, 138.6, 136.5, 136.3, 133.3, 132.5, 130.0, 129.5, 128.0, 120.5, 119.4, 111.9, 111.8, 111.0, 78.5, 42.0, 28.7, 25.3, 11.6, 11.5; IR (diffuse reflectance) 3399, 1688, 1479, 1365, 1349, 1311, 1298, 1155, 1144, 1134, 1124, 1074, 729, 691, 611 cm$^{-1}$; HRMS (FAB) calcd for $C_{22}H_{26}N_2O_4S$+H 415.1691, found 415.1692; Anal. Calcd for $C_{22}H_{26}N_2O_4S$: C, 63.74; H, 6.32; N, 6.76. Found: C, 63.43; H. 6.40; N, 6.59.

Step 2: Preparation of N-methyl-2-[2-methyl-5-(phenylsulfonyl)-1H-indol-3-yl]ethanamine A solution of tert-butyl 2-[2-methyl-5-(phenylsulfonyl)-1H-indol-3-yl]ethylcarbamate (0.46 g, 1.10 mmol) in THF (2.0 mL) was added to a slurry of LiAlH$_4$ (0.47 g, 12.3 mmol) in THF (4.0 mL) and the mixture was heated to reflux for 6.5 hours. The reaction was cooled to room temperature and quenched with water (12.0 mL) and 15% NaOH (12.0 mL). The mixture was filtered through diatomaceous earth and the filtrate was concentrated in vacuo. The residue was extracted with CH$_2$Cl$_2$, dried over MgSO$_4$ and concentrated in vacuo and recrystallized from EtOAc/hexane to give 0.17 g (46%) of a white solid as the title compound: mp 164.6–166.0° C.; $^1$H NMR (400 MHz, Acetone-d$_6$) δ 8.20 (d, J=1.6 Hz, 1H), 7.97–7.95 (m, 2H), 7.59–7.52 (m, 4H), 7.42 (d, J=8.6 Hz, 1H), 2.93–2.90 (m, 2H), 2.78–2.74 (m, 2H), 2.41 (s, 3H), 2.36 (s, 3H); $^{13}$C NMR (100 MHz, Acetone-d$_6$) δ 145.0, 138.6, 135.9, 133.3, 132.4, 130.0, 129.5, 127.9, 120.3, 119.6, 111.8, 53.5, 36.7, 25.2, 11.6; IR (diffuse reflectance) 3028, 3021, 2939, 2909, 2870, 2843, 1449, 1307, 1301, 1152, 1087, 750, 719, 692, 623 cm$^{-1}$; HRMS (FAB) calcd for $C_{18}H_{20}N_2O_2S$+H 329.1324, found 329.1326; Anal. Calcd for $C_{18}H_{20}N_2O_2S$: C, 65.83; H, 6.14; N, 8.53. Found: C, 65.47; H, 6.21; N, 8.38.

Example 4

2-[1,2-dimethyl-5-(phenylsulfonyl)-1H-indol-3-yl]ethanamine hydrochloride

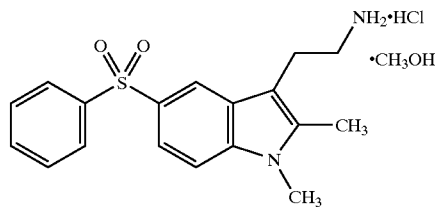

Step 1: Preparation of tert-butyl 2-[1,2-dimethyl-5-(phenylsulfonyl)-1H-indol-3-yl]ethylcarbamate Following the general procedure of EXAMPLE 1 (Step 2) and making non-critical variations, the title compound was prepared a colorless solid (85%): mp 151.4–155.4° C.; $^1$H NMR (400 MHz, CDCl$_3$) δ 8.16 (d, J=1.7 Hz, 1H), 7.96–7.93 (m, 2H), 7.65 (dd, J=8.6, 1.7 Hz, 1H), 7.50–7.42 (m, 3H), 7.30 (d, J=8.7 Hz, 1H), 4.59 (br, 1H), 3.67 (s, 3H), 3.32–3.30 (m, 2H), 2.95–2.93 (m, 2H), 2.38 (s, 3H), 1.43 (br, 9H); $^{13}$C NMR (100 MHz, CDCl$_3$) δ 155.9, 143.2, 138.6, 136.9, 132.4, 131.3, 129.0, 127.4, 127.2, 120.0, 118.7, 110.0, 109.2, 79.2, 41.2, 29.9, 28.4, 24.8, 10.4; IR (diffuse reflectance) 1696, 1499, 1451, 1300, 1266, 1249, 1185, 1152, 1098, 1093, 796, 727, 693, 655, 606 cm$^{-1}$; HRMS (FAB) calcd for $C_{23}H_{28}N_2O_4S$+Na 451.1667, found 451.1651; Anal. Calcd for $C_{23}H_{28}N_2O_4S$: C, 64.46; H, 6.59; N, 6.54. Found: C, 64.36; H, 6.56; N, 6.54.

Step 2: Preparation of 2-(1,2-dimethyl-5-(phenylsulfonyl)-1H-indol-3-yl]ethanamine hydrochloride Following the general procedure of EXAMPLE 1 (Step 4) and making non-critical variations, the title compound was prepared as a colorless solid (69%): mp 155.0–158.3° C.; $^1$H NMR (400 MHz, DMSO-d$_6$) δ 8.22 (s, 1H), 8.10 (br, 3H), 7.95–7.93 (m, 2H), 7.64–7.55 (m, 5H), 4.14 (br, 1H), 3.69 (s, 3H), 3.17 (s, 3H), 3.09–3.05 (m, 2H), 3.00–2.92 (m, 2H), 2.40 (s, 3H); $^{13}$C NMR (100 MHz, DMSO-d$_6$) δ 142.8, 138.1, 138.1, 132.8, 130.6, 129.4, 126.7, 126.5, 119.2, 117.8, 110.2, 107.3, 48.5, 29.8, 21.7, 10.0; IR (diffuse reflectance) 3027, 3002, 2976, 2943, 2890, 1486, 1450, 1300, 1280, 1154, 1097, 726, 693, 652, 605 cm$^{-1}$; HRMS (FAB) calcd for $C_{18}H_{20}N_2O_2S$+H 329.1324, found 329.1321; Anal. Calcd for $C_{18}H_{20}N_2O_2S \cdot HCl \cdot CH_3OH$: C, 57.49; H, 6.35; N, 7.06. Found: C, 57.03; H, 6.38; N, 7.00.

Example 5

2-[1,2-dimethyl-5-(phenylsulfonyl)-1H-indol-3-yl]-N-methylethanamine hydrochloride

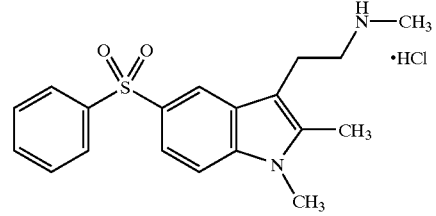

Step 1: Preparation of tert-butyl 2-[1,2-dimethyl-5-(phenylsulfonyl)-1H-indol-3-yl]ethyl(methyl)carbamate A solution of tert-butyl 2-[1,2-dimethyl-5-(phenylsulfonyl)-1H-indol-3-yl]ethylcarbamate (2.99 g, 6.98 mmol) in DMF (20.0 mL) was added to a 0° C.

suspension of 60% sodium hydride (0.75 g, 18.82 mmol) in DMF (5.0 mL) and stirred at room temperature for one hour. Methyl iodide (0.55 mL, 8.83 mmol) was added and the reaction was stirred at room temperature for 22 hours. The reaction was cooled to 0° C., quenched with water (10.0 mL) and filtered. The filtrate was concentrated in vacuo, combined with the previously filtered solid and partitioned between ethyl acetate and water. The layers were separated and the organic layer was washed with brine, dried over $MgSO_4$ and concentrated in vacuo and recrystallized from EtOAc/hexane to give 2.56 g (83%) of colorless crystals as the title compound: mp 147.1–149.0° C.; $^1$H NMR (400 MHz, DMSO-$d_6$) δ 8.15–8.10 (m, 1H), 7.92 (d, J=7.1 Hz, 2H), 7.62–7.53 (m, 5H), 3.67 (s, 3H), 3.32 (m, 2H), 2.91–2.88 (m, 2H), 2.79 (br, 3H), 2.33 (br, 3H), 1.35–0.99 (2 br, 9H); $^{13}$C NMR (100 MHz, DMSO-$d_6$) δ 154.4, 142.9, 138.0, 137.1, 132.7, 130.4, 129.3, 126.9, 126.7, 119.0, 117.7, 109.9, 109.4, 77.7, 48.8, 33.7, 29.7, 27.9, 27.4, 22.0, 9.8; IR (diffuse reflectance) 1692, 1482, 1446, 1364, 1303, 1219, 1192, 1164, 1152, 1140, 1095, 725, 689, 655, 609 $cm^{-1}$; HRMS (FAB) calcd for $C_{24}H_{30}N_2O_4S+H$ 443.2004, found 443.2025. Anal. Calcd for $C_{24}H_{30}N_2O_4S$: C, 65.13; H. 6.83; N, 6.33. Found: C, 65.06; H, 6.86; N, 6.33.

Step 2: Preparation of 2-[1,2-dimethyl-5-(phenylsulfonyl)-1H-indol-3-yl]-N-methylethanamine hydrochloride Following the general procedure of EXAMPLE 1 (Step 4) and making non-critical variations, the title compound was prepared as a colorless solid (85%): mp 266.8–268.2° C.; $^1$H NMR (400 MHz, DMSO-$d_6$) δ 8.99 (br, 2H), 8.23 (s, 1H), 7.96–7.93 (m, 2H), 7.64–7.55 (m, 5H), 3.69 (s, 3H), 3.14–3.10 (m, 2H), 3.01–2.97 (m, 2H), 2.57 (s, 3H), 2.41 (s, 3H); $^{13}$C NMR (100 MHz, DMSO-$d_6$) δ 142.8, 138.1, 138.1, 132.8, 130.7, 129.4, 126.7, 126.4, 119.2, 117.9, 110.2, 107.1, 48.6, 32.2, 29.8, 20.4, 10.0; IR (diffuse reflectance) 2969, 2954, 2931, 2785, 2739, 2726, 1306, 1292, 1157, 1100, 833, 726, 688, 652, 619 $cm^{-1}$; HRMS (FAB) calcd for $C_{19}H_{22}N_2O_2S+H$ 343.1480, found 343.1497; Anal. Calcd for $Cl_{19}H_{22}N_2O_2S \cdot HCl$: C, 60.22; H, 6.12; N, 7.39. Found: C, 60.26; H, 6.23; N, 7.39.

Example 6

2-[1,2-dimethyl-5-(phenylsulfonyl)-1H-indol-3-yl]-N,N-dimethylethanamine

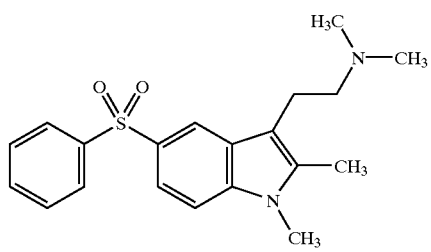

A solution of 2-[1,2-dimethyl-5-(phenylsulfonyl)-1H-indol-3-yl]-N-methylethanamine hydrochloride (0.34 g, 0.91 mmol) and formaldehyde (37%, 1.4 mL, 18.80 mmol) in acetonitrile was treated with sodium cyanoborohydride (0.92 g, 14.69 mmol) in portions. The reaction was stirred at room temperature for 2.5 days. The reaction mixture was concentrated in vacuo and the residue partitioned between $CHCl_3$ and $NH_4OH$. The layers were separated and the aqueous layer was extracted with $CHCl_3$. The organic layers were combined, washed with brine, dried over $MgSO_4$ and filtered. The filtrate was concentrated in vacuo and subjected to column chromatography (silica gel, 75% EtOAc/hexane) to give 0.08 g (23%) of white solid as the title compound: mp 169.6–171.9° C.; $^1$H NMR (400 MHz, DMSO-$d_6$) δ 8.07 (s, 1H), 7.93–7.91 (m, 2H), 7.63–7.55 (m, 5H), 3.67 (s, 3H), 2.86–2.82 (m, 2H), 2.41–2.37 (m, 2H), 2.36 (s, 3H), 2.24 (s, 6H); $^{13}$C NMR (100 MHz, DMSO-$d_6$) δ 142.8, 137.9, 136.8, 132.7, 130.3, 129.3, 126.8, 126.7, 118.7, 118.0, 110.2, 110.0, 59.9, 44.9, 29.7, 21.8, 9.9; IR (diffuse reflectance) 2936, 2776, 2760, 1482, 1449, 1377, 1303, 1285, 1153, 1143, 1094, 729 (s), 687, 651, 619 $cm^{-1}$; HRMS (FAB) calcd for $C_{20}H_{24}N_2O_2S+H$ 357.1637, found 357.1649; Anal. Calcd for $C_{20}H_{24}N_2O_2S$: C, 65.72; H, 6.88; N, 7.66. Found: C, 65.52; H, 6.71; N, 7.73.

Example 7

2-{1-methyl-5-[(4-methylphenyl)sulfonyl]-1H-indol-3-yl}ethanamine hydrochloride

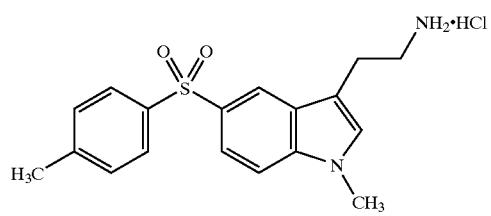

Step 1: Preparation of 2-{5-[(4-methylphenyl)sulfonyl]-1H-indol-3-yl}ethanamine

Following the general procedure of EXAMPLE 1 (Step 1) and making non-critical variations, the title compound was prepared as a brown solid (30%): mp 137.1–140.5° C.; $^1$H NMR (400 MHz, DMSO-$d_6$) δ 11.45 (br, 1H), 8.19 (d, J=1.2 Hz, 1H), 7.80 (d, J=8.2 Hz, 2H), 7.55 (dd, J=8.6, 1.6 Hz, 1H), 7.52 (d, J=8.6 Hz, 1H), 7.38–7.36 (m, 3H), 2.33 (s, 3H); $^{13}$C NMR (100 MHz, DMSO-d6) δ 143.2, 140.0, 138.1, 130.8, 129.8, 126.8, 126.5, 125.6, 119.5, 118.9, 114.3, 112.3, 42.4, 28.5, 20.8; IR (diffuse reflectance) 3112, 3014, 2950, 2941, 2917, 2889, 2861, 2833, 1307, 1297, 1289, 1156, 1133, 1106, 674 $cm^{-1}$; HRMS (FAB) calcd for $C_{17}H_{18}N_2O_2S+H$ 315.1167, found 315.1171; Anal. Calcd for $C_{17}H_{18}N_2O_2S \cdot 0.25H_2O$: C, 64.03; H, 6.01; N, 8.78. Found: C, 64.02; H, 5.83; N, 8.58.

Step 2: Preparation of tert-butyl 2-{5-[(4-methylphenyl)sulfonyl]-1H-indol-3-yl}ethylcarbamate Following the general procedure of EXAMPLE 1 (Step 2) and making non-critical variations, the title compound was prepared as a brown foam (91%): $^1$H NMR (400 MHz, DMSO-$d_6$) δ 11.40 (s, 1H), 8.19 (s, 1H), 7.80 (d, J=8.2 Hz, 2H), 7.54 (dd, J=8.6, 1.6 Hz, 1H), 7.51 (d, J=8.6 Hz, 1H), 7.38–7.36 (m, 3H), 6.93 (br, 1H), 3.21–3.18 (m, 2H), 2.87–2.83 (m, 2H), 2.33 (s, 3H), 1.38 (s, 9H); $^{13}$C NMR (100 MHz, DMSO-$d_6$) δ 155.5, 143.2, 139.9, 138.0, 130.9, 129.8, 126.8, 126.7, 125.6, 119.5, 118.9, 113.8, 112.3, 77.4, 40.6, 28.2, 25.0, 20.8; IR (diffuse reflectance) 1691, 1517, 1366, 1310, 1300, 1287, 1251, 1169, 1150 (s), 1108, 1080, 814, 707, 692, 675 $cm^{-1}$; HRMS (FAB) calcd for $C_{22}H_{26}N_2O_4S+H$ 414.1613, found 414.1607.

Step 3: Preparation of tert-butyl 2-{1-methyl-5-[(4-methylphenyl)sulfonyl]-1H-indol-3-yl}ethylcarbamate Following the general procedure of EXAMPLE 1 (Step 3) and making non-critical variations, the title compound was prepared as a colorless solid (61%): mp 143.9–147.5° C.; $^1$H NMR (400 MHz, $CDCl_3$) δ 8.25 (d, J=1.7 Hz, 1H), 7.82 (d, J=8.3 Hz, 2H), 7.71 (dd, J=8.7, 1.7 Hz, 1H), 7.34 (d, J=8.7 Hz, 1H), 7.26 (m, 2H), 7.00 (s, 1H), 4.60 (br, 1H), 3.76 (s, 3H), 3.44 (m, 2H), 2.97–2.93 (m, 2H), 2.36 (s, 3H), 1.43 (s, 9H); $^{13}$C NMR (100 MHz, CDCl$_3$) δ 155.9, 143.3, 140.1, 138.8, 131.9, 129.7, 129.0, 127.5, 127.3, 120.7, 119.9, 113.9, 109.9, 79.3, 40.8, 33.0, 28.4, 25.5, 21.5; IR (diffuse reflectance) 3413, 1713, 1518, 1365, 1313, 1299, 1266, 1250, 1172, 1158, 1145, 1098, 806, 665, 624 cm$^{-1}$; HRMS (FAB) calcd for C$_{23}$H$_{28}$N$_2$O$_4$S+H 429.1848, found 429.1840; Anal. Calcd for C$_{23}$H$_{28}$N$_2$O$_4$S: C, 64.46; H, 6.59; N, 6.54. Found: C, 64.31; H, 6.60; N, 6.46.

Step 4: Preparation of 2-{1-methyl-5-[(4-methylphenyl)sulfonyl]-1H-indol-3-yl}ethanamine hydrochloride Following the general procedure of EXAMPLE 1 (Step 4) and making non-critical variations, the title compound was prepared as a colorless solid (85%): mp 186.3–190.2° C.; $^1$H NMR (400 MHz, DMSO-d$_6$) δ 8.26 (d, J=1.2 Hz, 1H), 8.05 (br, 3H), 7.81 (d, J=8.3 Hz, 2H), 7.66–7.60 (m, 2H), 7.46 (s, 1H), 7.39 (m, 2H), 3.78 (m, 3H), 3.05 (br, 4H), 2.34 (s, 3H); $^{13}$C NMR (100 MHz, DMSO-d$_6$) δ 143.3, 139.8, 138.3, 131.3, 130.8, 129.8, 126.8, 126.6, 119.8, 118.9, 110.9, 32.6, 22.4, 20.8; IR (diffuse reflectance) 3021, 3008, 3000, 2990, 2978, 2934, 1488, 1313, 1303, 1290, 1144, 1097, 708, 682, 666 cm$^{-1}$; HRMS (FAB) calcd for C$_{18}$H$_{20}$N$_2$O$_2$S+H 329.1324, found 329.1318; Anal. Calcd for C$_{18}$H$_{20}$N$_2$O$_2$S.HCl.H$_2$O: C, 56.46; H, 6.06; N, 7.32. Found: C, 56.75; H, 6.01; N, 7.34.

Example 8

N-methyl-2-{1-methyl-5-[(4-methylphenyl)sulfonyl]-1H-indol-3-yl}ethanamine hydrochloride

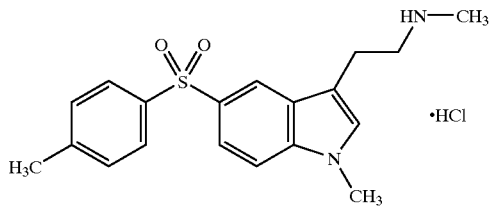

Step 1: Preparation of tert-butyl methyl(2-{1-methyl-5-[(4-methylphenyl)sulfonyl]-1H-indol-3-yl}ethyl)carbamate Following the general procedure of EXAMPLE 5 (Step 1) and making non-critical variations, the title compound was prepared as a yellow solid (84%): mp 142.9–144.8° C.; $^1$H NMR (400 MHz, DMSO-d$_6$) δ 8.18 (br, 1H), 7.82 (d, J=7.7 Hz, 1H), 7.63–7.56 (m, 2H), 7.37 (d, J=8.2 Hz, 2H), 7.31 (s, 1H), 3.76 (s, 3H), 3.41–3.39 (m, 2H), 2.93–2.89 (m, 2H), 2.79 (s, 3H), 2.33 (s, 3H), 1.37–1.03 (br, 9H); $^{13}$C NMR (100 MHz, DMSO-d$_6$) δ 154.5, 143.2, 139.9, 138.3, 131.0, 130.3, 129.8, 127.0, 126.8, 119.6, 118.9, 113.0, 110.7, 77.8, 48.9, 33.4, 32.5, 27.5, 22.6, 20.8; IR (diffuse reflectance) 1686, 1485, 1398, 1365, 1311, 1298, 1221, 1172, 1149, 1099, 821, 800, 679, 642, 613 cm$^{-1}$; HRMS (FAB) calcd for C$_{24}$H$_{30}$N$_2$O$_4$S+H 443.2004, found 443.2006; Anal. Calcd for C$_{24}$H$_{30}$N$_2$O$_4$S: C, 65.13; H, 6.83; N, 6.33. Found: C, 65.07; H, 6.82; N, 6.28.

Step 2: Preparation of N-methyl-2-{1-methyl-5-[(4-methylphenyl)sulfonyl]-1H-indol-3-yl}ethanamine hydrochloride Following the general procedure of EXAMPLE 1 (Step 4) and making non-critical variations, the title compound was prepared as a colorless solid (78%): mp 275.0–277.6° C.; $^1$H NMR (400 MHz, DMSO-d$_6$) δ 9.01 (br, 2H), 8.29 (d, J=1.2 Hz, 1H), 7.83 (d, J=8.3 Hz, 2H), 7.66–7.60 (m, 2H), 7.47 (s, 1H), 7.38 (d, J=8.2 Hz, 2H), 3.79 (s, 3H), 3.14 (s, 4H), 2.58 (s, 3H), 2.34 (s, 3H); $^{13}$C NMR (100 MHz, DMSO-d$_6$) δ 143.3, 139.8, 138.3, 131.3, 130.7, 129.8, 126.9, 126.5, 119.9, 119.0, 110.9, 110.7, 48.3, 32.6, 32.2, 20.9, 20.8; IR (diffuse reflectance) 2976, 2940, 2863, 2792, 2761, 2728, 1487, 1314, 1305, 1147, 1102, 814, 710, 694, 660 cm$^{-1}$; HRMS (FAB) calcd for C$_{19}$H$_{22}$N$_2$O$_2$S+H 343.1480, found 343.1491; Anal. Calcd for C$_{19}$H$_{22}$N$_2$O$_2$S.HCl: C, 60.22; H, 6.12; N, 7.39. Found: C, 60.12; H, 6.14; N, 7.36.

Example 9

2-{2-methyl-5-[(4-methylphenyl)sulfonyl]-1H-indol-3-yl}ethanamine hydrochloride

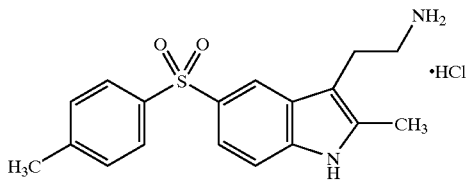

Following the general procedure of EXAMPLE 1 (Step 1) and making non-critical variations, the title compound was prepared by recrystallizing the crude product from MeOH/EtOAc to as a brown solid (64%): mp>275° C.; $^1$H NMR (400 MHz, DMSO-d$_6$) δ 11.60 (s, 1H), 8.15 (d, J=1.4 Hz, 1H), 8.04 (br, 3H), 7.79 (d, J=8.2 Hz, 2H), 7.50 (dd, J=8.6, 1.9 Hz, 1H), 7.43 (d, J=8.5 Hz, 1H), 7.38 (d, J=8.2 Hz, 2H), 3.04–3.00 (m, 2H), 2.94 (m, 2H), 2.38 (s, 3H), 2.34 (s, 3H); $^{13}$C NMR (100 MHz, DMSO-d$_6$) δ 143.2, 140.0, 137.2, 136.3, 130.9, 129.8, 127.4, 126.7, 119.1, 117.5, 111.3, 107.1, 39.2, 21.5, 20.8, 11.2; IR (diffuse reflectance) 3225, 3217, 3212, 3194, 3182, 3047, 3023, 2998, 2954, 1310, 1299, 1149, 711, 666, 663 cm$^{-1}$; HRMS (FAB) calcd for C$_{18}$H$_{20}$N$_2$O$_2$S+H 329.1324, found 329.1317; Anal. Calcd for C$_{18}$H$_{21}$N$_2$ClO$_2$S: C, 59.25; H, 5.80; N, 7.68. Found: C, 58.94; H, 5.83; N, 7.56.

Example 10

2-{1,2-dimethyl-5-[(4-methylphenyl)sulfonyl]-1H-indol-3-yl}ethanamine hydrochloride

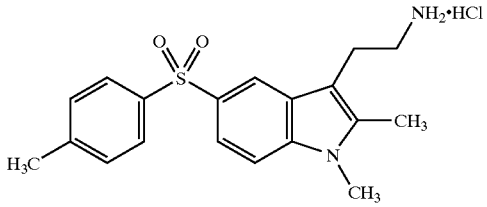

Step 1: Preparation of tert-butyl 2-{2-methyl-5-[(4-methylphenyl)sulfonyl]-1H-indol-3-yl}ethylcarbamate Following the general procedure of EXAMPLE 1 (Step 2) and making non-critical variations, the title compound was prepared by recrystallizing the crude product from EtOAc as a colorless solid (94%): mp 133.8–137.8° C.; $^1$H NMR (400 MHz, DMSO-d$_6$) δ 11.35 (s, 1H), 8.07 (s, 1H), 7.78 (d, J=8.2 Hz, 2H), 7.46 (dd, J=8.6, 1.6 Hz, 1H), 7.39–7.35 (m, 3H), 6.87 (br, 1H), 3.09–3.04 (m, 2H), 2.80–2.77 (m, 2H), 2.33 (s, 6H), 1.36 (s, 9H); $^{13}$C NMR (100 MHz, DMSO-d$_6$) δ 155.4, 143.1, 140.1, 137.1, 135.5, 130.6, 129.7, 127.8, 126.7, 118.8, 117.6, 111.1, 109.4, 77.3, 41.7, 28.1, 24.0, 20.8, 11.1; IR (diffuse reflectance) 1691, 1475, 1365, 1347, 1311, 1307, 1297, 1287, 1173, 1153, 1123, 1075, 714, 666, 657 cm$^{-1}$; HRMS (FAB) calcd for C$_{23}$H$_{28}$N$_2$O$_4$S+H 429.1848, found 429.1852; Anal. Calcd for C$_{23}$H$_{28}$N$_2$O$_4$S.0.25H$_2$O: C, 63.79; H, 6.63; N, 6.47. Found: C, 63.85; H, 6.57; N, 6.35.

Step 2: Preparation of tert-butyl 2-{1,2-dimethyl-5-[(4-methylphenyl)sulfonyl]-1H-indol-3-yl}ethylcarbamate Following the general procedure of EXAMPLE 1 (Step 3) and making non-critical variations, the title compound was prepared as a colorless foam (67%): $^1$H NMR (400 MHz, DMSO-d$_6$) δ 8.10 (s, 1H), 7.79 (d, J=8.2 Hz, 2H), 7.53 (br, 2H), 7.36 (d, J=8.2 Hz, 2H), 6.86 (br, 1H), 3.67 (s, 3H), 3.07–3.02 (m, 2H), 2.83–2.80 (m, 2H), 2.35 (s, 3H), 2.33. (s, 3H), 1.36 (s, 9H); $^{13}$C NMR (100 MHz, DMSO-d$_6$) δ 155.5, 143.1, 140.1, 137.9, 137.2, 130.7, 129.7, 126.8, 126.7, 118.8, 117.7, 109.9, 109.5, 77.3, 40.9, 29.7, 28.1, 24.2, 20.8, 9.9; IR (diffuse reflectance) 1710, 1508, 1500, 1487, 1377, 1366, 1311, 1301, 1288, 1250, 1183, 1171, 1150, 1096, 682 (s) cm$^{-1}$; HRMS (FAB) calcd for C$_{24}$H$_{30}$N$_2$O$_4$ 442.1926, found 442.1933.

Step 3: Preparation of 2-{1,2-dimethyl-5-[(4-methylphenyl)sulfonyl]-1H-indol-3-yl}ethanamine hydrochloride Following the general procedure of EXAMPLE 1 (Step 4) and making non-critical variations, the title compound was prepared as a colorless solid (87%): mp 168–172° C.; $^1$H NMR (400 MHz, DMSO-d$_6$) δ 8.18 (s, 1H), 8.03 (br, 3H), 7.80 (d, J=8.3 Hz, 2H), 7.60–7.55 (m, 2H), 7.38 (d, J=8.2 Hz, 2H), 3.69 (s, 3H), 3.07–3.03 (m, 2H), 2.92–2.89 (m, 2H), 2.39 (s, 3H), 2.34 (s, 3H); $^{13}$C NMR (100 MHz, DMSO-d$_6$) δ 143.2, 140.0, 138.0, 137.9, 131.1, 129.8, 126.7, 126.4, 119.1, 117.6, 110.1, 107.2, 29.8, 21.7, 20.8, 10.0; IR (diffuse reflectance) 3563, 3025, 2958, 2925, 1484, 1376, 1310, 1297, 1287, 1149, 1096, 815, 712, 679, 662 cm$^{-1}$; HRMS (FAB) calcd for C$_{19}$H$_{22}$N$_2$O$_2$S+H 343.1480, found 343.1472; Anal. Calcd for C$_{19}$H$_{22}$N$_2$O$_2$S.HCl.0.75H$_2$O: C, 58.15; H, 6.04; N, 7.14. Found: C, 58.04; H, 6.59; N, 6.82.

Example 11

2-{1,2-dimethyl-5-[(4-methylphenyl)sulfonyl]-1H-indol-3-yl}-N-methylethanamine hydrochloride

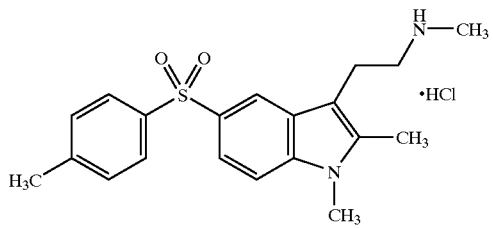

Step 1: Preparation of tert-butyl 2-{1,2-dimethyl-5-[(4-methylphenyl)sulfonyl]-1H- indol-3-yl}ethyl(methyl)carbamate Following the general procedure of EXAMPLE 5 (Step 1) and making non-critical variations, the title compound was prepared as a light brown solid (50%): mp 129.1–132.9° C.; $^1$H NMR (400 MHz, DMSO-d$_6$) δ 8.07 (s, 1H), 7.79 (d, J=7.9 Hz, 2H), 7.54 (m, 2H), 7.36 (d, J=8.0 Hz, 2H), 3.67 (s, 3H), 3.30 (m, 2H), 2.89 (t, J=6.9 Hz, 2H), 2.78–2.73 (2 s, 3H), 2.35 (br, 3H), 2.33 (s, 3H), 1.35–1.02 (2 s, 9H); $^{13}$C NMR (100 MHz, DMSO-d$_6$) δ 154.4, 143.1, 140.0, 137.9, 130.8, 129.7, 126.7, 118.9, 117.5, 109.9, 109.3, 77.7, 48.8, 33.7, 29.6, 27.9, 22.0, 20.8, 9.8; IR (diffuse reflectance) 2970, 1692, 1491, 1363, 1312, 1300, 1289, 1183, 1172, 1149, 1139, 1095, 814, 687, 676 cm$^{-1}$; HRMS (FAB) calcd for C$_{25}$H$_{32}$N$_2$O$_4$S 456.2083, found 456.2077; Anal. Calcd for C$_{25}$H$_{32}$N$_2$O$_4$S: C, 65.76; H, 7.06; N, 6.14. Found: C, 65.49; H, 7.08; N, 6.15.

Step 2: Preparation of 2-{1,2-dimethyl-5-[(4-methylphenyl)sulfonyl]-1H-indol-3-yl}-N-methylethanamine hydrochloride Following the general procedure of EXAMPLE 1 (Step 4) and making non-critical variations, the title compound was prepared as a colorless solid (98%): mp 259.7–262.3° C.; $^1$H NMR (400 MHz, DMSO-d$_6$) δ 8.93 (br, 2H), 8.20 (s, 1H), 7.80 (d, J=8.3 Hz, 2H), 7.60–7.54 (m, 2H), 7.38 (d, J=8.2 Hz, 2H), 3.69 (s, 3H), 3.13–3.09 (m, 2H), 2.99 (m, 2H), 2.57 (br, 3H), 2.41 (s, 3H), 2.33 (s, 3H); $^{13}$C NMR (100 MHz, DMSO-d$_6$) δ 143.2, 140.0, 138.0, 137.9, 131.1, 129.8, 126.8, 126.3, 119.1, 117.6, 110.1, 107.0, 48.6, 32.2, 29.8, 20.7, 20.4, 10.0; IR (diffuse reflectance) 2949, 2742, 1489, 1453, 1382, 1310, 1300, 1287, 1152, 1140, 1097, 815, 711, 682, 660 cm$^{-1}$; HRMS (FAB) calcd for C$_{20}$H$_{24}$N$_2$O$_2$S+H 357.1637, found 357.1659; Anal. Calcd for C$_{20}$H$_{24}$N$_2$O$_2$S.HCl: C, 61.13; H, 6.41; N, 7.13. Found: C, 61.02; H, 6.50; N, 7.08

Example 12

2-(2-methyl-5-{[4-(trifluoromethyl)phenyl]sulfonyl}-1H-indol-3-yl)ethanamine hydrochloride

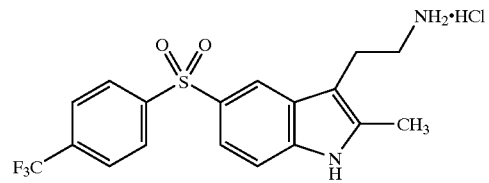

Following the general procedure of EXAMPLE 1 (Step 1) and making non-critical variations, the title compound was prepared by recrystallizing the crude product from MeOH/CHCl$_3$ as an off white solid (60%): mp>275° C.; $^1$H NMR (400 MHz, DMSO-d$_6$) δ 11.70 (s, 1H), 8.24 (d, J=1.6 Hz, 1H), 8.15 (d, J=8.2 Hz, 2H), 8.04 (br, 3H), 7.97 (d, J=8.4 Hz, 2H), 7.56 (dd, J=8.5, 1.7 Hz, 1H), 7.48 (d, J=8.6 Hz, 1H), 3.03–3.02 (m, 2H), 2.95 (m, 2H), 2.39 (s, 3H); $^{13}$C NMR (100 MHz, DMSO-d$_6$) δ 146.7, 137.6, 136.7, 132.9, 132.5, 132.2, 129.2, 127.7, 127.6, 127.3, 126.6, 126.6, 124.6, 121.9, 119.3, 118.3, 111.6, 107.3, 79.1, 21.5, 11.2; $^{19}$F NMR (376 MHz, DMSO-d$_6$) −62.13 (s); IR (diffuse reflectance) 3052, 1325, 1303, 1295, 1176, 1153, 1140, 1132, 1112, 1086, 1062, 717, 640, 619, 604 cm$^{-1}$; HRMS (FAB) calcd for C$_{18}$H$_{17}$F$_3$N$_2$O$_2$S+H 383.1041, found 383.1049; Anal. Calcd for C$_{18}$H$_{17}$F$_3$N$_2$O$_2$S.HCl.2.5H$_2$O: C, 46.60; H, 4.99; N, 6.04. Found: C, 46.20; H, 3.91; N, 5.82.

Example 13

2-(1,2-dimethyl-5-{[4-(trifluoromethyl)phenyl]sulfonyl}-1H-indol-3-yl)ethanamine hydrochloride

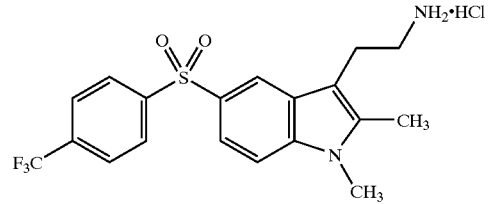

Step 1: Preparation of tert-butyl 2-(2-methyl-5-{[4-(trifluoromethyl)phenyl]sulfonyl}-1H-indol-3-yl)ethylcarbamate Following the general procedure of EXAMPLE 1 (Step 2) and making non-critical variations, the title compound was prepared by recrystallizing the crude product from EtOAc/Et$_2$O as a colorless solid (80%): mp 161.9–163.9° C.; $^1$H NMR (400 MHz, DMSO-d$_6$) 67 11.43 (s, 1H), 8.15–8.13 (m, 3H), 7.95 (d, J=8.4 Hz, 2H), 7.53 (dd, J=8.5, 1.5 Hz, 1H), 7.44 (d, J=8.5 Hz, 1H), 6.86 (br, 1H), 3.11–3.06 (m, 2H), 2.82–2.79 (m, 2H), 2.35 (s, 3H) 1.34 (s, 9H); $^{13}$C NMR (100 MHz, DMSO-d$_6$) δ 155.5, 146.8, 137.5, 135.9, 135.7, 132.5, 132.2, 128.8, 128.1, 127.7, 127.3, 126.6, 124.6, 121.9, 119.2, 119.0, 118.4, 111.4, 109.7, 77.3, 41.2, 28.1, 24.0, 11.1; $^{19}$F NMR (376 MHz, DMSO-d$_6$) −62.17 (s); IR (diffuse reflectance) 3364, 1695, 1525, 1325, 1305, 1292, 1270, 1173, 1155, 1140, 1109, 1096, 1063, 714, 622 cm$^{-1}$; HRMS (FAB) calcd for C$_{23}$H$_{25}$F$_3$N$_2$O$_4$S 482.1487, found 482.1488; Anal. Calcd for C$_{23}$H$_{25}$F$_3$N$_2$O$_4$S: C, 57.25; H, 5.22; N, 5.81. Found: C, 57.21; H, 5.31; N, 5.77

Step 2: Preparation of tert-butyl 2-(1,2-dimethyl-5-{[4-(trifluoromethyl)phenyl]sulfonyl}-1H-indol-3-yl)ethylcarbamate Following the general procedure of EXAMPLE 1 (Step 3) and making non-critical variations, the title compound was prepared as a colorless solid (59%): mp 124.5–128.520 C.; $^1$H NMR (400 MHz, DMSO-d$_6$) δ 8.18 (s, 1H), 8.13 (d, J=8.2 Hz, 2H), 7.95 (d, J=8.4 Hz, 2H), 7.60 (m, 2H), 6.85 (br, 1H), 3.69 (s, 3H), 3.09–3.04 (m, 2H), 2.85–2.82 (m, 2H), 2.36 (s, 3H), 1.34 (s, 9H); $^{13}$C NMR (100 MHz, DMSO-d$_6$) δ 155.5, 146.8, 138.3, 137.6, 132.5, 132.2, 129.0, 127.7, 127.3, 127.1, 126.6, 124.6, 121.9, 119.0, 118.4, 110.2, 109.8, 77.3, 40.8, 29.7, 28.1, 27.5, 24.2, 9.9; $^{19}$F NMR (376 MHz, DMSO-d$_6$) δ −62.2 (s); IR (diffuse reflectance) 1693, 1513, 1368, 1322, 1304, 1292, 1170, 1152, 1132, 1107, 1098, 1062, 714, 660, 615 cm$^{-1}$; HRMS (FAB) calcd for C$_{24}$H$_{27}$F$_3$N$_2$O$_4$S 496.1643, found 496.1637; Anal. Calcd for C$_{24}$H$_{27}$F$_3$N$_2$O$_4$S: C, 58.05; H, 5.48; N, 5.64. Found: C, 57.96; H, 5.56; N, 5.60.

Step 3: Preparation of 2-(1,2-dimethyl-5-{[4-(trifluoromethyl)phenyl]sulfonyl}-1H-indol-3-yl)ethanamine hydrochloride Following the general procedure of EXAMPLE 1 (Step 4) and making non-critical variations, the title compound was prepared as a colorless solid (79%): mp>280° C.; $^1$H NMR (400 MHz, DMSO-d$_6$) δ 8.27 (s, 1H), 8.15 (d, J=8.3 Hz, 2H), 8.02 (br, 3H), 7.97 (d, J=8.5 Hz, 2H), 7.64 (s, 2H), 3.70 (s, 3H), 3.08–3.04 (m, 2H), 2.94–2.90 (m, 2H), 2.40 (s, 3H); $^{13}$C NMR (100 MHz, DMSO-d$_6$) δ 146.6, 138.4, 132.6, 132.2, 131.9, 129.3, 127.7, 127.3, 126.6, 124.6, 121.9, 119.3, 118.3, 110.4, 107.4, 29.8, 21.7, 10.0; $^{19}$F NMR (376 MHz, DMSO-d$_6$) δ −62.1 (s); IR (diffuse reflectance) 2828, 1321, 1305, 1189, 1154, 1137, 1099, 1062, 1016, 842, 804, 716, 663, 613, 600 cm$^{-1}$; HRMS (FAB) calcd for C$_{19}$H$_{19}$F$_3$N$_2$O$_2$S+H 397.1197, found 397.1206; Anal. Calcd for C$_{19}$H$_{19}$F$_3$N$_2$O$_2$S: C, 52.72; H, 4.66; N, 6.47. Found: C, 52.66; H, 4.74; N, 6.43.

Example 14

2-(1,2-dimethyl-5-{[4-(trifluoromethyl)phenyl]sulfonyl}-1H-indol-3-yl)-N-methylethanamine hydrochloride

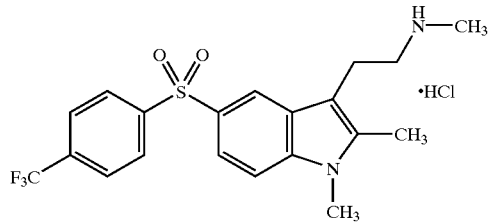

Step 1: Preparation of tert-butyl 2-(1,2-dimethyl-5-{[4-(trifluoromethyl)phenyl]sulfonyl}-1H-indol-3-yl)ethyl(methyl)carbamate Following the general procedure of EXAMPLE 5 (Step 1) and making non-critical variations, the title compound was prepared as a yellow solid (95%): mp 140.6–144.3° C. $^1$H NMR (400 MHz, DMSO-d$_6$) δ 8.18 (br, 1H), 8.06 (d, J=8.2 Hz, 2H), 7.72 (d, J=8.3 Hz, 2H), 7.66 (dd, J=8.7 Hz, 1.8 Hz, 1H), 7.33 (d, J=8.7 Hz, 1H), 3.67 (s, 3H), 3.40–3.37 (m, 2H), 2.94 (m, 2H), 2.83 (br, 3H), 2.37 (br, 3H), 1.58–1.16 (m, 9H); $^{13}$C NMR (100 MHz, DMSO-d$_6$) δ 155.5, 146.9, 138.8, 134.2, 133.9, 130.1, 127.7, 126.2, 126.1, 124.6, 121.9, 120.0, 119.0, 110.5, 109.4, 79.1, 49.6, 34.6, 31.9, 29.9, 29.7, 22.9, 22.7, 10.3; $^{19}$F NMR (376 MHz, DMSO-d$_6$) δ −63.6 (s); IR (diffuse reflectance) 1693, 1326, 1322, 1309, 1221, 1192, 1170, 1154, 1135, 1098, 1064, 725, 712, 659, 613 cm$^{-1}$; HRMS (FAB) calcd for C$_{25}$H$_{29}$F$_3$N$_2$O$_4$S+H 511.1878, found 511.1873; Anal. Calcd for C$_{25}$H$_{29}$F$_3$N$_2$O$_4$S: C, 58.81; H, 5.72; N, 5.49. Found: C, 58.79; H, 5.82; N, 5.50.

Step 2: Preparation of 2-(1,2-dimethyl-5-{[4-(trifluoromethyl)phenyl]sulfonyl}-1H-indol-3-yl)-N-methylethanamine hydrochloride Following the general procedure of EXAMPLE 1 (Step 4) and making non-critical variations, the title compound was prepared as a colorless solid (71%): mp 189.1–193.7° C.; $^1$H NMR (400 MHz, DMSO-d$_6$) δ 8.92 (br, 2H), 8.29 (s, 1H), 8.16 (d, J=8.4 Hz, 2H), 7.97 (d, J=8.5 Hz, 2H), 7.64 (s, 2H), 3.71 (s, 3H), 3.14–3.10 (m, 2H), 3.01 (m, 2H), 2.58 (br, 3H), 2.41 (s, 3H); $^{13}$C NMR (100 MHz, DMSO-d$_6$) δ 147.0, 138.7, 132.9, 132.6, 132.2, 129.7, 128.1, 127.7, 127.0, 126.9, 124.9, 122.2, 119.7, 118.7, 110.8, 107.6, 48.9, 48.8, 32.5, 30.2, 20.8, 10.4; $^{19}$F NMR (376 MHz, DMSO-d$_6$) δ −62.1 (s); IR (diffuse reflectance) 2952, 1322, 1304, 1291, 1189, 1177, 1157, 1140, 1122, 1109, 1098, 1060, 717, 657, 623 cm$^{-1}$; HRMS (FAB) calcd for C$_{20}$H$_{21}$F$_3$N$_2$O$_2$S+H 411.1354, found 411.1350; Anal. Calcd for C$_{20}$H$_{21}$F$_3$N$_2$O$_2$S.HCl: C, 53.75; H, 4.96; N, 6.27. Found: C, 53.27; H, 5.06; N, 6.17.

Example 15

2-{5-[(3-methoxyphenyl)sulfonyl]-2-methyl-1H-indol-3-yl}ethanamine hydrochloride

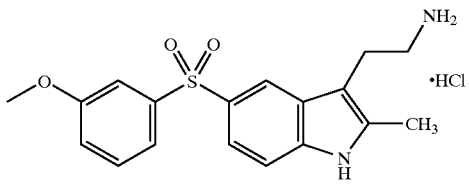

Following the general procedure of EXAMPLE 1 (Step 1) and making non-critical variations, the title compound was prepared by recrystalizing the crude product from MeOH/EtOAc as a light brown solid (75%): mp 300–302° C.; $^1$H NMR (400 MHz, DMSO-$d_6$) δ 11.60 (s, 1H), 8.19 (s, 1H), 8.00 (br, 2H), 7.56–7.41 (m, 5H), 7.19–7.16 (m, 1H), 3.81 (s, 3H), 3.02–3.00 (m, 2H), 2.95–2.93 (m, 2H), 2.38 (s, 3H); $^{13}$C NMR (100 MHz, DMSO-$d_6$) δ 159.4, 144.1, 137.3, 136.4, 130.7, 130.4, 127.5, 119.3, 118.8, 118.5, 117.8, 111.6, 111.4, 107.2, 55.6, 48.5, 21.5, 11.2; IR (diffuse reflectance) 3493, 3072, 3051, 3006, 2977, 2862, 1620, 1595, 1582, 1475, 1299, 1288, 1240, 1154, 1145, 1114, 1035, 1026 cm$^{-1}$; HRMS (FAB) calcd for $C_{18}H_{20}N_2O_3S$+H 345.1273, found 345.1274; Anal. Calcd for $C_{18}H_{20}N_2O_3S$·HCl: C, 56.76; H, 5.56; N, 7.36. Found: C, 56.86; H, 5.61; N, 7.34.

Example 16

2-{5-[(3-methoxyphenyl)sulfonyl]-1,2-dimethyl-1H-indol-3-yl}ethanamine hydrochloride

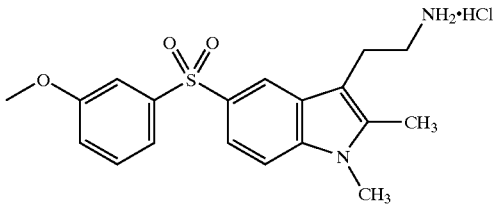

Step 1: Preparation of tert-butyl 2-{5-[(3-methoxyphenyl)sulfonyl]-2-methyl-1H-indol-3-yl}ethylcarbamate Following the general procedure of EXAMPLE 1 (Step 2) and making non-critical variations, the title compound was prepared by recrystallizing the crude product from CH$_2$Cl$_2$/EtOAc as a colorless solid (53%): mp 169.8–172.9° C.; $^1$H NMR (400 MHz, DMSO-$d_6$) δ 11.40 (s, 1H), 8.11 (s, 1H), 7.50 (dd, J=8.6, 1.7 Hz, 1H), 7.48–7.46 (m, 2H), 7.40–7.38 (m, 2H), 7.18–7.15 (m, 1H), 7.86 (br, 1H), 3.80 (s, 3H), 3.09–3.04 (m, 2H), 2.81–2.78 (m, 2H), 2.34 (s, 3H), 1.36 (s, 9H); $^{13}$C NMR (100 MHz, DMSO-$d_6$) δ 159.4, 155.4, 144.2, 137.2, 135.6, 130.6, 130.1, 127.9, 118.9, 118.8, 118.4, 117.9, 111.5, 111.1, 109.5, 77.3, 55.5, 28.1, 27.7, 24.0, 11.1; IR (diffuse reflectance) 3380, 3350, 1696, 1524, 1481, 1302, 1292, 1267, 1250, 1174, 1149, 1125, 701, 685, 628 cm$^{-1}$; HRMS (FAB) calcd for $C_{23}H_{28}N_2O_5S$+H 445.1797, found 445.1794; Anal. Calcd for $C_{23}H_{28}N_2O_5S$: C, 62.14; H, 6.35; N, 6.30. Found: C, 62.21; H, 6.46; N, 6.28.

Step 2: Preparation of tert-butyl 2-{5-[(3-methoxyphenyl)sulfonyl]-1,2-dimethyl-1H-indol-3-yl}ethylcarbamate Following the general procedure of EXAMPLE 1 (Step 3) and making non-critical variations, the title compound was prepared by recrystallizing the crude product from EtOAc/hexanes as a lavender solid (66%): mp 114.7–122.4° C.; $^1$H NMR (400 MHz, DMSO-$d_6$) δ 8.14 (br, 1H), 7.57–7.53 (m, 2H), 7.48–7.46 (m, 2H), 7.41 (br, 1H), 7.18–7.17 (m, 1H), 6.86 (br, 1H), 3.80 (s, 3H), 3.67 (s, 3H), 3.06–3.05 (m, 2H), 2.84–2.83 (m, 2H), 2.35 (s, 3H), 1.36 (s, 9H); $^{13}$C NMR (100 MHz, DMSO-$d_6$) δ 159.4, 155.5, 144.2, 138.0, 137.2, 130.6, 130.2, 126.9, 118.9, 118.8, 118.5, 118.0, 111.5, 109.9, 109.6, 77.3, 55.6, 40.9, 29.7, 28.1, 24.2, 9.9; IR (diffuse reflectance) 1715, 1520, 1481, 1311, 1303, 1285, 1242, 1184, 1166, 1145, 1040, 702, 685, 659, 613 cm$^{-1}$; HRMS (FAB) calcd for $C_{24}H_{30}N_2O_5S$+H 458.1875, found 458.1877; Anal. Calcd for $C_{24}H_{30}N_2O_5S$: C, 62.86; H, 6.59; N, 6.11. Found: C, 62.69; H, 6.56; N, 6.08.

Step 3: Preparation of 2-{5-[(3-methoxyphenyl)sulfonyl]-1,2-dimethyl-1H-indol-3-yl}ethanamine hydrochloride Following the general procedure of EXAMPLE 1 (Step 4) and making non-critical variations, the title compound was prepared as a colorless solid (73%): mp 269.5–272.4° C.; $^1$H NMR (400 MHz, DMSO-$d_6$) δ 8.23 (s, 1H), 8.05 (br, 3H), 7.63–7.58 (m, 2H), 7.49–7.48 (m, 2H), 7.42 (m, 1H), 7.19–7.16 (m, 1H), 3.81 (s, 3H), 3.69 (s, 3H), 3.08–3.04 (m, 2H), 2.93–2.89 (m, 2H), 2.39 (s, 3H); $^{13}$C NMR (100 MHz, DMSO-$d_6$) δ 159.4, 144.1, 138.2, 138.1, 130.7, 130.6, 126.5, 119.3, 118.8, 118.5, 117.9, 111.6, 110.2, 107.3, 55.6, 29.8, 21.7, 10.0; IR (diffuse reflectance) 2943, 2835, 2792, 1484, 1454, 1377, 1307, 1250, 1152, 1095, 792, 697, 681, 654, 610 cm$^{-1}$; HRMS (FAB) calcd for $C_{19}H_{22}N_2O_3S$+H 359.1429, found 359.1430; Anal. Calcd for $C_{19}H_{22}N_2O_3S$·HCl: C, 57.79; H, 5.87; N, 7.09. Found: C, 57.77; H, 5.94; N, 7.08.

Example 17

2-{5-[(3-methoxyphenyl)sulfonyl]-1,2-dimethyl-1H-indol-3-yl}-N-methylethanamine hydrochloride

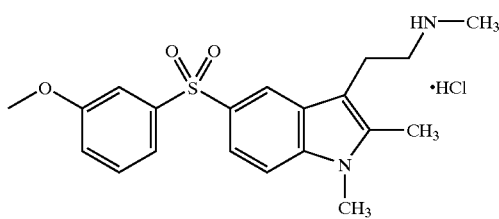

Step 1: Preparation of tert-butyl 2-{5-[(3-methoxyphenyl)sulfonyl]-1,2-dimethyl-1H-indol-3-yl}ethyl(methyl)carbamate Following the general procedure of EXAMPLE 5 (Step 1) and making non-critical variations, the title compound was prepared as a colorless solid (84%): mp 123.2–127.1° C.; $^1$H NMR (400 MHz, DMSO-$d_6$) δ 8.10 (m, 1H), 7.60–7.54 (m, 2H), 7.47–7.46 (m, 2H), 7.40 (m, 1H), 7.17–7.15 (m, 1H), 3.80 (s, 3H), 3.67 (s, 3H), 3.30 (m, 2H), 2.91–2.88 (m, 2H), 2.78–2.73 (m, 3H), 2.33 (m, 3H) 1.34 (br, 3H), 0.99 (br, 6H); $^{13}$C NMR (100 MHz, DMSO-$d_6$) δ 159.4, 154.4, 144.1, 138.1, 137.1, 130.6, 130.3, 126.9, 119.1, 118.9, 118.5, 117.8, 111.5, 109.9, 109.4, 77.7, 55.5, 48.8, 33.7, 29.7, 22.0, 9.8; IR (diffuse reflectance) 1693, 1481, 1306, 1294, 1285, 1239, 1190, 1167, 1137, 1044, 700, 683, 657, 611, 604 cm$^{-1}$; HRMS (FAB) calcd for $C_{25}H_{32}N_2O_5S$+H 472.2032, found 472.2044; Anal. Calcd for $C_{25}H_{32}N_2O_5S$: C, 63.54; H, 6.82; N, 5.93. Found: C, 63.56; H, 6.82; N, 5.89.

Step 2: Preparation of 2-{5-[(3-methoxyphenyl)sulfonyl]-1,2-dimethyl-1H-indol-3-yl}-N-methylethanamine hydrochloride Following the general procedure of EXAMPLE 1 (Step 4) and making non-critical variations, the title compound was prepared as a colorless solid (100%): mp 192.4–196.0° C.; $^1$H NMR (400 MHz, DMSO-$d_6$) δ 8.96 (br, 2H), 8.25 (s, 1H), 7.63–7.58 (m, 2H), 7.49–7.46 (m, 2H), 7.43 (m, 1H), 7.20–7.16 (m, 1H), 3.82 (s, 3H), 3.69 (s, 3H), 3.14–3.10 (m, 2H), 2.99 (m, 2H), 2.57 (s, 3H), 2.41 (s, 3H); $^{13}$C NMR (100 MHz, DMSO-$d_6$) δ 159.4, 144.1, 138.1, 138.0, 130.6, 130.5, 126.4, 119.3, 118.9, 118.6, 118.0, 111.6, 110.2, 107.1, 55.6, 48.6, 32.2, 29.8, 20.5, 10.0; IR (diffuse reflectance) 2972, 2946, 1482, 1303 1287, 1250, 1241, 1151, 1036, 710, 698, 685, 657, 617, 608 cm$^{-1}$; HRMS (FAB) calcd for $C_{20}H_{24}N_2O_3S$+H 373.1586, found 373.1594; Anal. Calcd for $C_{20}H_{24}N_2O_3S$.HCl: C, 58.74; H, 6.16; N, 6.85. Found: C, 58.78; H, 6.22; N, 6.81.

Example 18

2-{5-[(3,5-difluorophenyl)sulfonyl]-2-methyl-1H-indol-3-yl}ethanamine hydrochloride

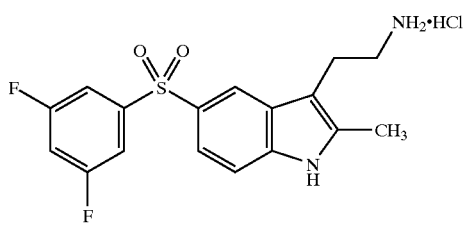

Following the general procedure of EXAMPLE 1 (Step 1) and making non-critical variations, the title compound was prepared by recrystallizing the crude product from MeOH/EtOAc as a light brown solid (62%): mp>280° C.; $^1$H NMR (400 MHz, DMSO-$d_6$) δ 11.65 (s, 1H), 8.27 (d, J=1.7 Hz, 1H), 8.08 (br, 3H), 7.73–7.68 (m, 2H), 7.63–7.58 (m, 2H), 7.48 (d, J=8.6 Hz, 1H), 3.07–3.03 (m, 2H), 2.98 (m, 2H), 2.40 (s, 3H); $^{13}$C NMR (100 MHz, DMSO-$d_6$) δ 163.5, 163.4, 161.0, 160.9, 146.4, 146.3, 146.2, 137.7, 136.7, 128.9, 127.7, 119.4, 118.6, 111.5, 110.8, 110.7, 110.6, 110.5, 108.9, 108.7, 108.4, 107.4, 39.3, 21.5, 11.2; $^{19}$F NMR (376 MHz, DMSO-$d_6$) –106.25 (m); IR (diffuse reflectance) 3192, 3152, 3085, 3046, 1606, 1445, 1303, 1290, 1156, 1140, 987, 699, 666, 644, 606 cm$^{-1}$; HRMS (FAB) calcd for $C_{17}H_{16}F_2N_2O_2S$+H 351.0979, found 351.0975; Anal. Calcd for $C_{17}H_{16}F_2N_2O_2S$.HCl: C, 52.78; H, 4.43; N, 7.24. Found: C, 52.57; H, 4.56; N, 7.13.

Example 19

2-{5-[(3,5-difluorophenyl)sulfonyl]-1,2-dimethyl-1H-indol-3-yl}ethanamine hydrochloride

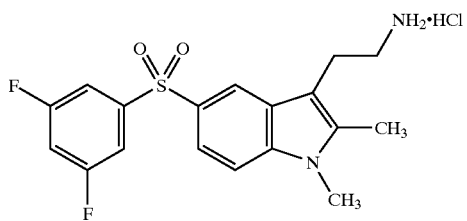

Step 1: Preparation of tert-butyl 2-{5-[(3,5-difluorophenyl)sulfonyl]-2-methyl-1H-indol-3-yl}ethylcarbamate Following the general procedure of EXAMPLE 1 (Step 2) and making non-critical variations, the title compound was prepared by recrystallizing the crude product from CH$_2$Cl$_2$/EtOAc as a colorless solid (80%): mp 201.4–203.8° C.; $^1$H NMR (400 MHz, DMSO-$d_6$) δ 11.43 (s, 1H), 8.18 (br, 1H), 7.69–7.68 (m, 2H), 7.61–7.56 (m, 2H), 7.43 (d, J=8.6 Hz, 1H), 6.85 (br, 1H), 3.09–3.06 (m, 2H), 2.83–2.79 (m, 2H), 2.34 (s, 3H), 1.34 (s, 9H); $^{13}$C NMR (100 MHz, DMSO-$d_6$) δ 163.5, 163.4, 161.0, 160.9, 155.5, 146.4, 146.3, 146.2, 137.7, 135.8, 128.6, 128.1, 119.1, 118.7, 111.3, 110.7, 110.6, 110.5, 110.4, 109.8, 108.9, 108.6, 108.3, 77.3, 59.7, 40.7, 28.1, 23.9, 11.1; $^{19}$F NMR (376 MHz, DMSO-$d_6$) δ –106.3 (m); IR (diffuse reflectance) 3366, 1693, 1605, 1531, 1440, 1317, 1297, 1175, 1151, 1127, 987, 866, 691, 669, 640 cm$^{-1}$; HRMS (FAB) calcd for $C_{22}H_{24}F_2N_2O_4S$+H 451.1503, found 451.1486; Anal. Calcd for $C_{22}H_{24}F_2N_2O_4S$: C, 58.65; H, 5.37; N, 6.22. Found: C, 58.46; H, 5.53; N, 6.09.

Step 2: Preparation of tert-butyl 2-{5-[(3,5-difluorophenyl)sulfonyl]-1,2-dimethyl-1H-indol-3-yl}ethylcarbamate Following the general procedure of EXAMPLE 1 (Step 3) and making non-critical variations, the title compound was prepared by recrystallizing the crude product from EtOAc/hexane as a colorless solid (83%): mp 181.5–185.8° C.; $^1$H NMR (400 MHz, CDCl$_3$) δ 8.14 (d, J=1.5 Hz, 1H), 7.65 (dd, J=8.7, 1.7 Hz, 1H), 7.48–7.45 (m, 2H), 7.34 (d, J=8.7 Hz, 1H), 6.94–6.89 (m, 1H), 4.60 (br, 1H), 3.70 (s, 3H), 3.32–3.31 (m, 2H), 2.96–2.94 (m, 2H), 2.40 (s, 3H), 1. 43 (s, 9H); $^{13}$C NMR (100 MHz, CDCl$_3$) δ 164.1, 164.0, 161.6, 161.4, 155.9, 146.8, 146.7, 146.6, 138.9, 137.3, 129.6, 127.6, 120.0, 119.1, 110.8, 110.7, 110.6, 110.2, 109.5, 108.2, 108.0, 107.7, 79.3, 41.2, 30.0, 28.4, 24.8, 10.5; $^{19}$F NMR (376 MHz, CDCl$_3$) δ –106.2 (m); IR (diffuse reflectance) 3368, 1716 , 1605, 1525, 1323, 1293, 1269, 1184, 1174, 1152, 1124, 986, 675, 668, 616 cm$^{-1}$; HRMS (FAB) calcd for $C_{23}H_{26}F_2N_2O_4S$+H 465.1659, found 465.1653; Anal. Calcd for $C_{23}H_{26}F_2N_2O_4S$.0.5H$_2$O: C, 58.33; H, 5.75; N, 5.92. Found: C, 58.18; H, 5.59; N, 5.89.

Step 3: Preparation of 2-{5-[(3,5-difluorophenyl)sulfonyl]-1,2-dimethyl-1H-indol-3-yl}ethanamine hydrochloride Following the general procedure of EXAMPLE 1 (Step 4) and making non-critical variations, the title compound was prepared as a colorless solid (83%): mp 288.6–290.5° C.; $^1$H NMR (400 MHz, DMSO-$d_6$) δ 8.28 (d, J=1.6 Hz, 1H), 8.00 (br, 3H), 7.71–7.58 (m, 5H), 3.71 (s, 3H), 3.09–3.05 (m, 2H), 2.96–2.93 (m, 2H), 2.40 (s, 3H); $^{13}$C NMR (100 MHz, DMSO-$d_6$) δ 163.5, 163.4, 161.0, 160.9, 146.3, 146.2, 146.1, 138.5, 138.4, 129.1, 126.6, 119.5, 118.6, 110.8, 110.7, 110.6, 110.5, 110.4, 109.0, 108.7, 108.4, 107.5, 29.8, 21.7, 10.0; 19 F NMR (376 MHz, DMSO-$d_6$) δ –106.2 (m); IR (diffuse reflectance) 2845, 2808, 1605, 1442, 1378, 1321, 1311, 1302, 1291, 1152, 1125, 986, 678, 666, 619 cm$^{-1}$; HRMS (FAB) calcd for $C_{18}H_{18}F_2N_2O_2S$+H 365.1135, found 365.1138; Anal. Calcd for $C_{18}H_{18}F_2N_2O_2S$.HCl: C, 53.93; H, 4.78; N, 6.99. Found: C, 53.90; H, 5.01; N, 6.81.

Example 20

2-{5-[(3,5-difluorophenyl)sulfonyl]-1,2-dimethyl-1H-indol-3-yl}-N-methylethanamine hydrochloride

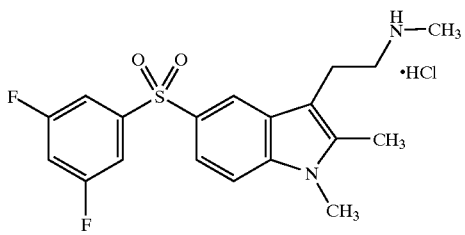

Step 1: Preparation of tert-butyl 2-{5-[(3,5-difluorophenyl)sulfonyl]-1,2-dimethyl-1H-indol-3-yl}ethyl(methyl)carbamate Following the general procedure of EXAMPLE 5 (Step 1) and making non-critical variations, the title compound was prepared as a colorless solid (76%): mp 158.5–161.6° C.; $^1$H NMR (400 MHz, DMSO-$d_6$) δ 8.14 (br, 1H), 7.69–7.56 (m, 5H), 3.69 (m, 5H), 3.30 (m, 2H), 2.92–2.89 (m, 2H), 2.79–2.74 (m, 3H), 1.33 (br, 3H), 0.91 (br, 6H); $^{13}$C NMR (100 MHz, DMSO-$d_6$) δ 163.5, 163.4, 161.0, 160.9, 154.4, 146.3, 138.4, 137.3, 128.8, 127.2, 119.2, 118.5, 110.7, 110.6, 110.5, 110.1, 109.8, 108.8, 108.5, 108.3, 77.5, 48.8, 33.6, 29.7, 27.9, 27.2, 21.9, 9.8; $^{19}$F NMR (376 MHz, DMSO-$d_6$) δ −106.5 (m); IR (diffuse reflectance) 1691, 1604, 1442, 1323, 1310, 1297, 1219, 1191, 1166, 1150, 1131, 988, 678, 664, 616 cm$^{-1}$; HRMS (FAB) calcd for $C_{24}H_{28}F_2N_2O_4S$+H 479.1816, found 479.1816; Anal. Calcd for $C_{24}H_{28}F_2N_2O_4S$: C, 60.24; H, 5.90; N, 5.85. Found: C, 60.19; H, 5.97; N, 5.80.

Step 2: Preparation of 2-{5-[(3,5-difluorophenyl)sulfonyl]-1,2-dimethyl-1H-indol-3-yl}-N-methylethanamine hydrochloride Following the general procedure of EXAMPLE 1 (Step 4) and making non-critical variations, the title compound was prepared as a colorless solid (78%): mp 253.5–257.8° C.; $^1$H NMR (400 MHz, DMSO-$d_6$) δ 8.99 (br, 2H), 8.23 (s, 1H), 7.96–7.93 (m, 2H), 7.64–7.55 (m, 5H), 3.69 (s, 3H), 3.14–3.10 (m, 2H), 3.01–2.97 (m, 2H), 2.57 (s, 3H), 2.41 (s, 3H); $^{13}$C NMR (100 MHz, DMSO-$d_6$) δ 142.8, 138.1, 138.1, 132.8, 130.7, 129.4, 126.7, 126.4, 119.2, 117.9, 110.2, 107.1, 48.6, 32.2, 29.8, 20.4, 10.0; IR (diffuse reflectance) 1604, 1455, 1440, 1321, 1307, 1297, 1151, 1128, 1087, 988, 866, 679, 667, 621, 612 cm$^{-1}$; HRMS (FAB) calcd for $C_{19}H_{20}F_2N_2O_2S$+H 379.1292, found 379.1302; Anal. Calcd for $C_{19}H_{20}F_2N_2O_2S$·HCl: C, 55.00; H, 5.10; N, 6.75. Found: C, 54.71; H, 5.27; N, 6.62.

Example 21

2-[2-methyl-5-(1-naphthylsulfonyl)-1H-indol-3-yl]ethanamine hydrochloride

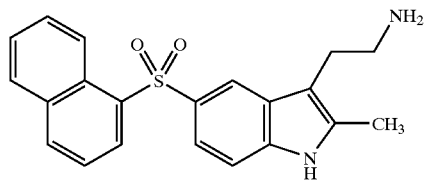

Following the general procedure of EXAMPLE 1 (Step 1) and making non-critical variations, the title compound was prepared as a colorless solid (16%): mp>280° C.; $^1$H NMR (400 MHz, DMSO-$d_6$) δ 11.60 (s, 1H), 8.71 (d, J=8.6 Hz, 1H), 8.40 (dd, J=7.2, 1.0 Hz, 1H), 8.35 (d, J=1.5 Hz, 1H), 8.25 (d, J=8.3 Hz, 1H), 8.05 (d, J=8.3 Hz, 1H), 8.03 (br, 3H), 7.76–7.72 (m, 1H), 7.69–7.65 (m, 1H), 7.62–7.58 (m, 1H), 7.45 (dd, J=8.6, 1.9 Hz, 1H), 7.39 (d, J=8.6 Hz, 1H), 3.06–3.02 (m, 2H), 2.93 (m, 2H), 2.35 (s, 3H); $^{13}$C NMR (100 MHz, DMSO-$d_6$) δ 137.2, 137.0, 136.4, 134.6, 133.7, 130.4, 129.1, 128.7, 128.1, 127.2, 127.2, 126.8, 124.8, 124.0, 119.2, 117.8, 111.3, 107.2, 21.6, 11.1; IR (diffuse reflectance) 3189, 3077, 3051, 3028, 2958, 2926, 1300, 1155, 1136, 1131, 805, 767, 702, 638, 615 cm$^{-1}$; HRMS (FAB) calcd for $C_{21}H_{20}N_2O_2S$+H 365.1324, found 365.1347; Anal. Calcd for $C_{21}H_{20}N_2O_2S$·HCl: C, 62.91; H, 5.28; N, 6.99. Found: C, 62.84; H, 5.32; N, 6.70.

Example 22

2-[1,2-dimethyl-5-(1-naphthylsulfonyl)-1H-indol-3-yl]ethanamine hydrochloride

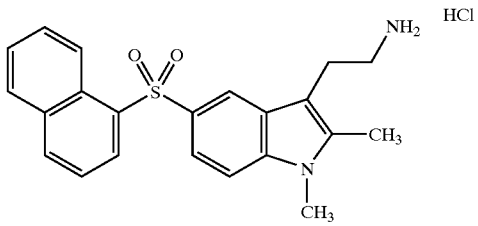

Step 1: Preparation of tert-butyl 2-{5-[1-naphthylsulfonyl]-2-methyl-1H-indol-3-yl}ethylcarbamate To a mixture of 2-[2-methyl-5-(1-naphthylsulfonyl)-1H-indol-3-yl]ethanamine hydrochloride (2.42 g, 6.03 mmol) and 4 N NaOH (3.77 mL) in dioxane (20.0 mL) was added di-tert-butyl dicarbonate (1.45 g, 6.63 mmol) at 0° C. After stirring at room temperature for 16 h, the reaction mixture was concentrated in vacuo. The aqueous residue was taken up to $H_2O$ and EtOAc and separated. The aqueous layer was extracted with EtOAc (2×). The combined EtOAc solutions was dried (MgSO$_4$) and filtered. The filtrate was concentrated in vacuo to dryness and the residue was subjected to column chromatography (silica gel, 50% EtOAc/heptane) to give 2.65 g (95%) of colorless solid as the title compound: mp 202–204° C. (CH$_2$Cl$_2$/heptane); IR (diffuse reflectance) 3079, 2954, 2925, 2869, 2854, 1689, 1507, 1458, 1393, 1300, 1167, 1155, 1146, 1120 cm$^{-1}$; $^1$H NMR (300 MHz, CDCl$_3$) δ 8.80 (d, J=8.5 Hz, 1H), 8.50–8.47 (m, 2H), 8.28 (d, J=1.4 Hz, 1H), 8.06 (d, J=8.2 Hz, 1H), 7.88 (d, J=7.7 Hz, 1H), 7.62–7.50 (m, 4H), 7.25 (d, J=8.6 Hz, 1H), 4.64 (br, 1H), 3.37–3.33 (m, 2H), 2.93–2.90 (m, 2H), 2.37 (s, 3H), 1.47 (s, 9H); $^{13}$C NMR (100 MHz, CDCl$_3$) δ 156.3, 137.7, 135.3, 134.9, 134.6, 132.4, 129.6, 129.3, 128.8, 128.5, 128.4, 127.1, 125.1, 124.8, 120.8, 119.0, 111.1, 110.9, 79.7, 41.3, 28.8, 25.0, 12.1; HRMS (FAB) calcd for $C_{26}H_{28}N_2O_4S$+Na 487.1667, found 487.1667; Anal. Calcd for $C_{26}H_{28}N_2O_4S$: C, 67.22; H, 6.07; N, 6.03. Found: C, 66.96; H, 6.26; N, 5.95.

Step 2: Preparation of tert-butyl 2-[5-(1-naphthylsulfonyl)-1,2-dimethyl-1H-indol-3-yl]ethylcarbamate Following the general procedure of EXAMPLE 1 (Step 3) and making non-critical variations, the title compound was obtained as a colorless solid (99%): mp 164–166° C. (CH$_2$Cl$_2$/heptane); IR (diffuse reflectance) 3386, 3059, 1707, 1610, 1593, 1565, 1506, 1391, 1367, 1305, 1183, 1168, 1154, 843, 826, 805 cm$^{-1}$; $^1$H NMR (400 MHz, CDCl$_3$) δ 8.80 (d, J=8.5 Hz, 1H), 8.49 (dd, J=7.4, 1.1 Hz, 1H), 8.30 (d, J=1.6 Hz, 1H), 8.05 (d, J=8.2 Hz, 1H), 7.88 (d, J=7.8 Hz, 1H), 7.68–7.50 (m, 4H), 7.26 (d, J=8.7 Hz, 1H), 4.64 (br, 1H), 3.65 (s, 3H), 3.36–3.33 (m, 2H), 2.99–2.94 (m, 2H), 2.39 (s, 3H), 1.48 (s, 9H).; $^{13}$C NMR (100 MHz, CDCl$_3$) δ 156.3, 138.9, 137.9, 137.3, 134.8, 134.6, 131.9, 129.5, 129.3, 128.8, 128.4, 127.5, 127.1, 125.1, 124.8, 120.4, 119.1, 110.3, 109.5, 79.7, 41.6, 30.3, 28.8, 25.2, 10.8; HRMS (FAB) calcd for $C_{27}H_{30}N_2O_4S$+Na 501.1830, found 501.1824; Anal. Calcd for $C_{27}H_{30}N_2O_4S$·0.5H$_2$O: C, 66.51; H, 6.41; N, 5.75. Found: C, 66.24 H, 6.22; N, 5.61.

Step 3: Preparation of 2-[5-(1-naphthylsulfonyl)-1,2-dimethyl-1H-indol-3-yl]ethanamine hydrochloride Following the general procedure of EXAMPLE 1 (Step 4) and making non-critical variations, the title compound was prepared as a colorless solid (100%): mp>175° C. (dec.); IR (diffuse reflectance) 3200–2500, 1608, 1568, 1566, 1505, 1484, 1456, 1297, 1154, 1135, 1121, 1075, 842, 807, 805, 771 cm$^{-1}$; $^1$H NMR (400 MHz, MeOH-d$_4$) δ 8.72 (d, J=8.5 Hz, 1H), 8.46 (dd, J=7.4, 1.1 Hz, 1H), 8.30 (d, J=1.6 Hz, 1H), 8.19 (d, J=8.3 Hz, 1H), 8.00–7.96 (m, 1H), 7.71–7.55 (m, 4H), 7.47 (d, J=8.7 Hz, 1H), 3.72 (s, 3H), 3.14–3.12 (m, 4H), 2.44 (s, 3H), $^{13}$C NMR (100 MHz, MeOH-d$_4$) δ 140.7, 139.9, 138.9, 136.4, 136.2, 133.2, 130.6, 130.5, 129.8, 129.3, 128.4, 128.3, 126.0, 125.9, 121.5, 119.4, 111.3, 108.4, 41.7, 30.6, 23.7, 10.7; HRMS (FAB) calcd for $C_{22}H_{22}N_2O_2S$+H 379.1480, found 379.1471; Anal. Calcd for $C_{22}H_{22}N_2O_2S \cdot HCl \cdot H_2O$: C, 61.03; H, 5.82; N, 6.47. Found: C, 60.79; H, 6.00; N, 6.40.

Example 23

2-[1,2-Dimethyl-5-(1-naphthylsulfonyl)-1H-indol-3-yl]-N-methylethanamine hydrochloride

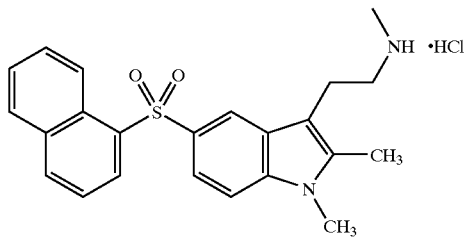

Step 1: Preparation of tert-butyl 2-[1,2-dimethyl-5-(1-naphthylsulfonyl)-1H-indol-3-yl]ethyl(methyl)carbamate Following the general procedure of EXAMPLE 5 (Step 1) and making non-critical variations, the title compound was prepared as a yellow solid (45%): mp 176–178° C.; $^1$H NMR (400 MHz, DMSO-d$_6$) δ 8.71 (d, J=8.3 Hz, 1H), 8.41 (d, J=7.2 Hz, 1H), 8.26–8.21 (m, 2H), 8.03 (d, J=7.9 Hz, 1H), 7.74–7.70 (m, 2H), 7.64–7.58 (m, 2H), 7.52 (m, 2H), 3.63 (s, 3H), 3.31–3.29 (m, 2H), 2.92–2.90 (m, 2H), 2.76 (br, 3H), 2.31 (br s, 3H), 1.37 (br, 3H), 0.95 (br, 6H); $^{13}$C NMR (100 MHz, DMSO-d$_6$) δ 154.3, 137.9, 137.2, 137.0, 134.5, 133.7, 130.4, 129.0, 128.7, 128.0, 127.3, 126.8, 126.7, 124.7, 124.0, 119.0, 117.7, 109.8, 109.4, 77.7, 48.8, 33.7, 29.6, 27.4, 22.0, 9.8; IR (diffuse reflectance) 2414, 2285, 1958, 1907, 1687, 1364, 1301, 1168, 1152, 1129, 804, 770, 687, 652, 610 cm$^{-1}$; HRMS (FAB) calcd for $C_{28}H_{32}N_2O_4S$+H 492.2083, found 492.2089; Anal. Calcd for $C_{28}H_{32}N_2O_4S$: C, 68.27; H, 6.55; N, 5.69. Found: C, 67.89 H, 6.53; N, 5.65.

Step 2: Preparation of 2-[1,2-dimethyl-5-(1-naphthylsulfonyl)-1H-indol-3-yl]-N-methylethanamine hydrochloride Following the general procedure of EXAMPLE 1 (Step 4) and making non-critical variations, the title compound was prepared as a yellow solid (69%): mp>141° C. (dec); $^1$H NMR (400 MHz, DMSO-d$_6$) δ 8.86 (br, 2H), 8.70 (d, J=8.6 Hz, 1H), 8.42–8.39 (m, 2H), 8.25 (d, J=8.2 Hz, 1H), 8.04 (d, J=7.9 Hz, 1H), 7.76–7.72 (m, 1H), 7.68–7.64 (m, 1H), 7.61–7.58 (m, 1H), 7.54–7.49 (m, 2H), 3.65 (s, 3H), 3.17–3.10 (m, 2H), 2.99 (m, 2H), 2.60–2.58 (m, 3H), 2.38 (s, 3H); $^{13}$C NMR (100 MHz, DMSO-d$_6$) δ 138.0, 137.9, 136.9, 134.6, 133.7, 130.6, 129.1, 128.7, 128.1, 127.2, 126.8, 126.1, 124.8, 124.0, 119.2, 117.9, 110.1, 107.0, 48.7, 32.3, 29.7, 20.5, 10.0; IR (diffuse reflectance) 3030, 2950, 2785, 2414, 1954, 1485, 1454, 1298, 1151, 1126, 807, 773, 688, 652, 606 cm$^{-1}$; HRMS (FAB) calcd for $C_{23}H_{24}N_2O_2S$+H 393.1637, found 393.1640; Anal. Calcd for $C_{23}H_{24}N_2O_2S \cdot HCl \cdot 0.9 H_2O$: C, 62.05; H, 6.07; N, 6.29. Found: C, 62.07; H, 6.14; N, 6.15.

5-HT$_6$ Receport Binding Assay

Growth of Cells and Membrane Preparation

Hela cells containing the cloned human 5-HT$_6$ receptor were acquired from Dr. David R. Sibley's laboratory in National Institute of Health (see Sibley, D. R., *J. Neurochemistry*, 66, 47–56, 1996). Cells were grown in high glucose Dulbecco's modified Eagle's medium, supplemented with L-glutamine, 0.5% sodium pyruvate, 0.3% penicillin-streptomycin, 0.025% G-418 and 5% Gibco fetal bovine serum and then were harvested, when confluent, in cold phosphate buffered saline.

Harvested intact cells were washed once in cold phosphate-buffered saline. The cells were pelleted and resuspended in 100 ml of cold 50 mM Tris, 5 mM EDTA and 5 mM EGTA, pH 7.4.Homogenization was with a Vir Tishear generator, 4 cycles for 30 seconds each at setting 50. The homogenized cells were centrifuged at 700 RPM (1000×g) for 10 minutes and the supernatant was removed. The pellet was resuspended in 100 ml of the above buffer and rehomogenized for 2 cycles. The rehomogenized cells were then centrifuged at 700 RPM (1000×g) for 10 minutes and the supernatant was removed. The combined supernatant (200 ml) was centrifuged at 23,000 RPM (80,000×g) for 1 hour in a Beckman Rotor (42.1 Ti). The membrane pellet was resuspended in 50-8-ml of assay buffer containing HEPES 20 mM, MgCl2 10 mM, NaCl 150 mM, EDTA 1 mM, pH 7.4 and stored frozen in aliqouts at −70° C.

5-HT$_6$ Receptor Binding Assay

The radioligand binding assay used [$^3$H]-lysergic acid diethylamide (LSD). The assay was carried out in Wallac 96-well sample plates by the addition of 11 μl of the test sample at the appropriate dilution (the assay employed 11 serial concentrations of samples run in duplicate), 11 μl of radioligand, and 178 μl of a washed mixture of WGA-coated SPA beads and membranes in binding buffer. The plates were shaken for about 5 minutes and then incubated at room temperature for 1 hour. The plates were then loaded into counting cassettes and counted in a Wallac MicroBeta Trilux scintillation counter.

Binding Constant (Ki) Determination

Eleven serial dilutions of test compounds were distributed to assay plates using the PE/Cetus Pro/Pette pipetter. These dilutions were, followed by radioligand and the bead-membrane mixture prepared as described above. The specifically bound cpm obtained were fit to a one-site binding model using GraphPad Prism ver. 3.0. Estimated IC$_{50}$ values were converted to Ki values using the Cheng-Prusoff equation (Cheng, Y. C. et al., *Biochem. Pharmacol.*, 22, 3099–108, 1973). The Ki values obtained as an average from the assay are shown in Table 1.

TABLE 1

| Example # | Ki (nM) |
|---|---|
| 1 | 1.5 nM |
| 2 | 38 nM |
| 3 | 37 nM |
| 4 | 4 nM |
| 5 | 9 nM |
| 6 | 1.8 nM |
| 7 | 3.3 nM |
| 8 | 7.6 nM |
| 9 | 308 nM |
| 10 | 22 nM |
| 11 | 15 nM |
| 12 | 146 nM |
| 13 | 36 nM |
| 14 | 18 nM |

TABLE 1-continued

| Example # | Ki (nM) |
|---|---|
| 15 | 209 nM |
| 16 | 3.4 nM |
| 17 | 10 nM |
| 18 | 66 nM |
| 19 | 5.6 nM |
| 20 | 4.6 nM |
| 21 | 0.9 nM |
| 22 | 3.1 nM |

What is claimed:

1. A compound of the Formula I:

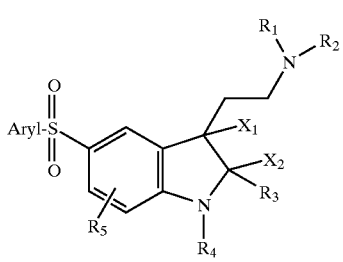

Formula I wherein

Aryl is phenyl, naphthyl, hetereoaromatic, substituted phenyl, substituted naphthyl, or substituted heteroaromatic;

$X_1$ and $X_2$ are both H or together form a bond between the C2 and the C3 carbon of the indole-ring of Formula I;

$R_1$ is H, $C_1$–$C_6$ alkyl, substituted alkyl, aryl, or —C(O)O-t-butyl;

$R_2$ is H, $C_1$–$C_6$ alkyl, substituted alkyl, aryl, or —C(O)O-t-butyl, provided that only one of $R_1$ and $R^2$ is —C(O)O-t-butyl;

$R_3$ is H, halogen, $C_1$–$C_6$ alkyl, substituted alkyl, or aryl;

$R_4$ is H, $C_1$–$C_6$ alkyl, substituted alkyl, or aryl;

Provided that $R_3$ and $R_4$ may not both be H;

$R_5$ is hydrogen, halogen, $C_1$–$C_4$ alkyl, substituted alkyl, —O—$C_1$–$C_6$ alkyl, substituted —O—$C_1$–$C_6$ alkyl, CN, $NO_2$, OH, —$N_3$, $NR_1R_2$, —C(O)$NR_1R_2$, —C(S)$NR_1R_2$, —O-aryl, or aryl; and pharmaceutically acceptable salts thereof.

2. The compound of claim 1, wherein $R_5$ is H.

3. The compound of claim 1, wherein $R_3$ is H or $C_1$–$C_6$ alkyl.

4. The compound of claim 1, wherein $R_4$ is H or $C_1$–$C_6$ alkyl.

5. The compound of claim 1, wherein aryl is phenyl or substituted phenyl.

6. The compound of claim 5, wherein aryl is a substituted phenyl.

7. The compound of claim 6, wherein the phenyl is substituted with 1–3 substituents selected from H, halogen, $C_1$–$C_4$ alkyl, —O—$C_1$–$C_4$ alkyl, and $CF_3$.

8. The compound of claim 7, wherein $R_5$ is H.

9. The compound of claim 8, wherein $R_3$ is H or $C_1$–$C_6$ alkyl.

10. The compound of claim 8, wherein $R_4$ is H or $C_1$–$C_6$ alkyl.

11. The compound of claim 9, wherein $R_4$ is H or $C_1$–$C_6$ alkyl.

12. The compound of claim 8, wherein $R_1$ and $R_2$ are independently H or $C_1$–$C_6$ alkyl.

13. The compound of claim 1, wherein $R_1$ or $R_2$ is —C(O)O-t-butyl.

14. The compound of claim 1, wherein aryl is naphthyl or substituted naphthyl.

15. The compound of claim 14, wherein $R_5$ is H.

16. The compound of claim 15, wherein $R_3$ is H or $C_1$–$C_6$ alkyl.

17. The compound of claim 15, wherein $R_4$ is H or $C_1$–$C_6$ alkyl.

18. The compound of claim 16, wherein $R_4$ is H or $C_1$–$C_6$ alkyl.

19. The compound of claim 1, wherein aryl is heteroaromatic or substituted heteroaromatic.

20. The compound of claim 19, wherein $R_5$ is H.

21. The compound of claim 20, wherein $R_3$ is H or $C_1$–$C_6$ alkyl.

22. The compound of claim 20, wherein $R_4$ is H or $C_1$–$C_6$ alkyl.

23. The compound of claim 21, wherein $R_4$ is H or $C_1$–$C_6$ alkyl.

24. The compound of claim 1, wherein $X_1$ and $X_2$ together form a bond between the C2 carbon and the C3 carbon of the indole-ring.

25. A compound of claim 1 selected from the group consisting of

2-[1-methyl-5-(phenylsulfonyl)-1H-indol-3-yl]ethanamine;

2-[2-methyl-5-(phenylsulfonyl)-1H-indol-3-yl]ethanamine;

N-methyl-2-[2-methyl-5-(phenylsulfonyl)-1H-indol-3-yl]ethanamine;

2-[1,2-dimethyl-5-(phenylsulfonyl)-1H-indol-3-yl]ethanamine;

2-[1,2-dimethyl-5-(phenylsulfonyl)-1H-indol-3-yl]-N-methylethanamine;

2-[1,2-dimethyl-5-(phenylsulfonyl)-1H-indol-3-yl]-N,N-dimethylethanamine;

2-{1-methyl-5-[(4-methylphenyl)sulfonyl]-1H-indol-3-yl}ethanamine;

N-methyl-2-{1-methyl-5-[(4-methylphenyl)sulfonyl]-1H-indol-3-yl}ethanamine;

2-{2-methyl-5-[(4-methylphenyl)sulfonyl]-1H-indol-3-yl}ethanamine;

2-{1,2-dimethyl-5-[(4-methylphenyl)sulfonyl]-1H-indol-3-yl}ethanamine;

2-{1,2-dimethyl-5-[(4-methylphenyl)sulfonyl]-1H-indol-3-yl}-N-methylethanamine;

2-(2-methyl-5-{[4-(trifluoromethyl)phenyl]sulfonyl}-1H-indol-3-yl)ethanamine;

2-(1,2-dimethyl-5-{[4-(trifluoromethyl)phenyl]sulfonyl}-1H-indol-3-yl)ethanamine;

2-(1,2-dimethyl-5-{[4-(trifluoromethyl)phenyl]sulfonyl}-1H-indol-3-yl)-N-methylethanamine;

2-{5-[(3-methoxyphenyl)sulfonyl]-2-methyl-1H-indol-3-yl}ethanamine

2-{5-[(3-methoxyphenyl)sulfonyl]-1,2-dimethyl-1H-indol-3-yl}ethanamine;

2-{5-[(3-methoxyphenyl)sulfonyl]-1,2-dimethyl-1H-indol-3-yl}-N-methylethanamine;

2-{5-[(3,5-difluorophenyl)sulfonyl]-2-methyl-1H-indol-3-yl}ethanamine;

2-{5-[(3,5-difluorophenyl)sulfonyl]-1,2-dimethyl-1H-indol-3-yl}ethanamine;

2-{5-[(3,5-difluorophenyl)sulfonyl]-1,2-dimethyl-1H-indol-3-yl}-N-methylethanamine;

2-[2-methyl-5-(1-naphthylsulfonyl)-1H-indol-3-yl]ethanamine;

2-[1,2-dimethyl-5-(1-naphthylsulfonyl)-1H-indol-3-yl]ethanamine; 2-[1,2-dimethyl-5-(1-naphthylsulfonyl)-1H- indol-3-yl]-N-methylethanamine; or a pharmaceutically acceptable salt thereof.

26. A compound selected from the group consisting of 2-[1-methyl-5-(phenylsulfonyl)-1H-indol-3-yl]ethanamine; 2-[1,2-dimethyl-5-(phenylsulfonyl)-1H-indol-3-yl]ethanamine; 2-{5-[(3-methoxyphenyl)sulfonyl]-1,2-dimethyl-1H-indol-3-yl}ethanamine; 2-{5-[(3,5-difluorophenyl)sulfonyl]-1,2-dimethyl-1H-indol-3-yl}-N-methylethanamine; 2-[2-methyl-5-(1-naphthylsulfonyl)-1H-indol-3-yl]ethanamine; 2-[1,2-dimethyl-5-(1-naphthylsulfonyl)-1H-indol-3-yl]ethanamine; or a pharmaceutically acceptable salt thereof.

27. A pharmaceutical composition comprising a compound according to claim 1.

28. A method for treating a disease or condition in a mammal, wherein the 5-HT$_6$ receptor is implicated, comprising administering to a mammal a therapeutically effective amount of compound according to claim 1.

29. The method according to claim 28, wherein the disease or condition is anxiety, depression, schizophrenia, Alzheimer's disease, stress-related disorder such as irritable bowel syndrome, panic, a phobia, obsessive compulsive disorder, obesity, post-traumatic stress syndrome, or epilepsy.

30. The method according to claim 28, wherein said compound is administered rectally, topically, orally, sublingually, or parenterally.

31. The method according to claim 28, wherein said compound is administered from about 0.001 to about 100 mg/kg of body weight of said mammal per day.

32. The method according to claim 28, wherein said compound is administered from about 0.1 to about 50 mg/kg of body weight of said mammal per day.

33. A method for treating a disease or condition in a mammal, wherein the 5-HT$_6$ receptor is implicated, comprising administering to a mammal a therapeutically effective amount of compound according to claim 26.

34. The method according to claim 33, wherein the disease or condition is anxiety, depression, schizophrenia, Alzheimer's disease, stress related disease, panic, a phobia, obsessive compulsive disorder, obesity, post-traumatic stress syndrome, or epilepsy.

35. The method according to claim 33, wherein said compound is administered rectally, topically, orally, sublingually, or parenterally.

36. The method according to claim 33, wherein said compound is administered from about 0.001 to about 100 mg/kg of body weight of said mammal per day.

37. The method according to claim 33, wherein said compound is administered from about 0.1 to about 50 mg/kg of body weight of said mammal per day.

38. A compound according to claim 1, selected from the group consisting of 2-[1-methyl-5-(phenylsulfonyl)-1H-indol-3-yl]ethanamine; 2-[1,2-dimethyl-5-(phenylsulfonyl)-1H-indol-3-yl]-N-methylethanamine; 2-[1,2-dimethyl-5-(phenylsulfonyl)-1H-indol-3-yl]ethanamine; 2-{5-[(3,5-difluorophenyl)sulfonyl]-1,2-dimethyl-1H-indol-3-yl}ethanamine; 2-{5-[(3,5-difluorophenyl)sulfonyl]-1,2-dimethyl-1H-indol-3-yl}-N-methylethanamine; 2-[2-methyl-5-(1-naphthylsulfonyl)-1H-indol-3-yl]ethanamine; and pharmaceutically acceptable salt thereof, wherein the compound includes an isotopic label.

39. The compound of claim 38, wherein the compound includes at least one atom selected from Carbon-11, Nitrogen-13, Oxygen-15, and Fluorine-18.

40. A method of performing positron emission tomography comprising:
incorporating an isotopically labeled compound into tissue of a mammal, wherein the isotopically labeled compound is selected from 2-[1-methyl-5-(phenylsulfonyl)-1H-indol-3-yl]ethanamine; 2-[1,2-dimethyl-5-(phenylsulfonyl)-1H-indol-3-yl]-N-methylethanamine; 2-[1,2-dimethyl-5-(phenylsulfonyl)-1H-indol-3-yl]ethanamine; 2-{5-[(3,5-difluorophenyl)sulfonyl]-1,2-dimethyl-1H-indol-3-yl}ethanamine; 2-{5-[(3,5-difluorophenyl)sulfonyl]-1,2-dimethyl-1H-indol-3-yl}-N-methylethanamine; 2-[2-methyl-5-(1-naphthylsulfonyl)-1H-indol-3-yl]ethanamine; and pharmaceutically acceptable salts thereof, and each compound includes at least one atom selected from Carbon-11, Nitrogen-13, Oxygen-15, and Fluorine-18.

41. A method of performing nuclear magnetic resonance imaging comprising:
incorporating a compound into tissue of a mammal, wherein the compound is selected from 2-{5-[(3,5-difluorophenyl)sulfonyl]-1,2-dimethyl-1H-indol-3-yl}ethanamine; 2-{5-[(3,5-difluorophenyl)sulfonyl]-1,2-dimethyl-1H-indol-3-yl}-N-methylethanamine, pharmaceutically acceptable salts thereof, and each of the compounds contains at least one $^{19}$F atom.

42. A compound according to claim 13 selected from the group consisting of
tert-butyl 2-[5-(phenylsulfonyl)-1H-indol-3-yl]ethylcarbamate;
tert-butyl 2-[1-methyl-5-(phenylsulfonyl)-1H-indol-3-yl]ethylcarbamate;
tert-butyl 2-[2-methyl-5-(phenylsulfonyl)-1H-indol-3-yl]ethylcarbamate;
tert-butyl 2-[1,2-dimethyl-5-(phenylsulfonyl)-1H-indol-3-yl]ethylcarbamate;
tert-butyl 2-[1,2-dimethyl-5-(phenylsulfonyl)-1H-indol-3-yl]ethyl(methyl)carbamate;
tert-butyl 2-{5-[(4-methylphenyl)sulfonyl]-1H-indol-3-yl}ethylcarbamate;
tert-butyl 2-{1-methyl-5-[(4-methylphenyl)sulfonyl]-1H-indol-3-yl}ethylcarbamate;
tert-butyl methyl(2-{1-methyl-5-[(4-methylphenyl)sulfonyl]-1H-indol-3-yl}ethyl)carbamate,
tert-butyl 2-{2-methyl-5-[(4-methylphenyl)sulfonyl]-1H-indol-3-yl}ethylcarbamate;
tert-butyl 2-{1,2-dimethyl-5-[(4-methylphenyl)sulfonyl]-1H-indol-3-yl}ethylcarbamate;
tert-butyl 2-{1,2-dimethyl-5-[(4-methylphenyl)sulfonyl]-1H-indol-3-yl}ethyl(methyl)carbamate;
tert-butyl 2-(2-methyl-5-{[4-(trifluoromethyl)phenyl]sulfonyl}-1H-indol-3-yl)ethylcarbamate;
tert-butyl 2-(1,2-dimethyl-5-{[4-(trifluoromethyl)phenyl]sulfonyl}-1H-indol-3-yl)ethylcarbamate;
tert-butyl 2-(1,2-dimethyl-5-{[4-(trifluoromethyl)phenyl]sulfonyl}-1H-indol-3-yl)ethyl(methyl)carbamate;
tert-butyl 2-{5-[(3-methoxyphenyl)sulfonyl]-2-methyl-1H-indol-3-yl}ethylcarbamate;
tert-butyl 2-{5-[(3-methoxyphenyl)sulfonyl]-1,2-dimethyl-1H-indol-3-yl}ethylcarbamate;
tert-butyl 2-{5-[(3-methoxyphenyl)sulfonyl]-1,2-dimethyl-1H-indol-3-yl}ethyl(methyl)carbamate;
tert-butyl 2-{5-[(3,5-difluorophenyl)sulfonyl]-2-methyl-1H-indol-3-yl}ethylcarbamate;
tert-butyl 2-{5-[(3,5-difluorophenyl)sulfonyl]-1,2-dimethyl-1H-indol-3-yl}ethylcarbamate;
tert-butyl 2-{5-[(3,5-difluorophenyl)sulfonyl]-1,2-dimethyl-1H-indol-3-yl}ethyl(methyl)carbamate;

tert-butyl 2-{5-[1-naphthylsulfonyl]-2-methyl-1H-indol-3-yl}ethylcarbamate;
tert-butyl 2-[5-(1-naphthylsulfonyl)-1,2-dimethyl-1H-indol-3-yl]ethylcarbamate and
tert-butyl 2-[1,2-dimethyl-5-(1-naphthylsulfonyl)-1H-indol-3-yl]ethyl(methyl)carbamate.

43. A process for preparing a compound of claim 1 having the Formula 15

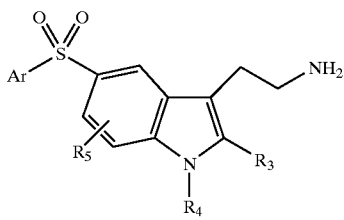

Formula 15 and pharmaceutically acceptable salts thereof, which comprises deprotecting a compound having the formula 10

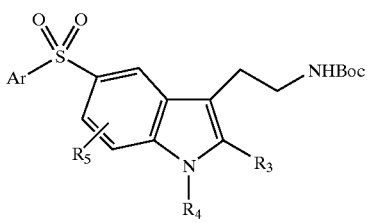

Formula 10 wherein
Aryl is phenyl, naphthyl, hetereoaromatic, substituted phenyl, substituted naphthyl, or substituted heteroaromatic;
$X_1$ and $X_2$ together form a bond between the C2 and the C3 carbon of the indole-ring of Formula I;
$R_3$ is H, halogen, $C_1$–$C_6$ alkyl, substituted alkyl, or aryl;
$R_4$ is H, $C_1$–$C_6$ alkyl, substituted alkyl, or aryl;
Provided that $R_3$ and $R_4$ may not both be H;
$R_5$ is hydrogen, halogen, $C_1$–$C_4$ alkyl, substituted alkyl, —$OC_1$–$C_6$ alkyl, substituted —$OC_1$–$C_6$ alkyl, CN, $NO_2$, OH, —$N_3$, $NR_1R_2$, —$C(O)NR_1R_2$, —$C(S)NR_1R_2$, —O-aryl, or aryl; and pharmaceutically acceptable salts thereof.

44. A process for preparing a compound of claim 1 having the Formula 12

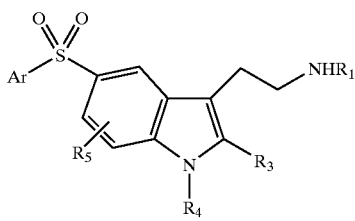

Formula 12 and pharmaceutically acceptable salts thereof, which comprises deprotecting a compound having the formula 11

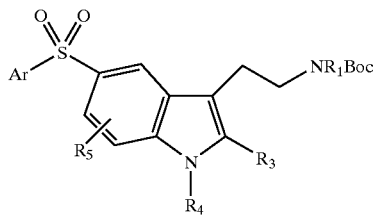

Formula 11 wherein
Aryl is phenyl, naphthyl, hetereoaromatic, substituted phenyl, substituted naphthyl, or substituted heteroaromatic;
$R_1$ is H, $C_1$–$C_6$ alkyl, substituted alkyl or aryl;
$R_3$ is H, halogen, $C_1$–$C_6$ alkyl, substituted alky or aryl;
$R_4$ is H, $C_1$–$C_6$ alkyl, substituted alkyl or aryl;
Provided that $R_3$ and $R_4$ may not both be H;
$R_5$ is hydrogen, halogen, $C_1$–$C_4$ alkyl, substituted alkyl, —$OC_1$–$C_6$ alkyl, substituted —$OC_1$–$C_6$ alkyl, CN, $NO_2$, OH, —$N_3$, $NR_1R_2$, —$C(O)NR_1R_2$, —$C(S)NR_1R_2$, —O-aryl or aryl; and pharmaceutically acceptable salts thereof.

45. A process for preparing a compound of claim 1 having the Formula 13

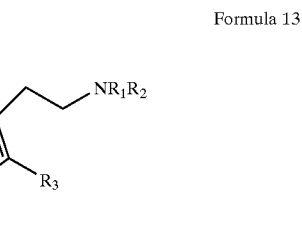

Formula 13 and pharmaceutically acceptable salts thereof, which comprises subjecting a compound having the Formula 12

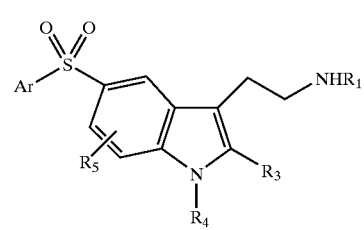

Formula 12 to reductive amination, wherein
Aryl is phenyl, naphthyl, hetereoaromatic, substituted phenyl, substituted naphthyl, or substituted heteroaromatic;
$R_2$ is H, $C_1$–$C_6$ alkyl, substituted alkyl, or aryl;
$R_3$ is H, halogen, $C_1$–$C_6$ alkyl, substituted alkyl, or aryl;
$R_4$ is H, $C_1$–$C_6$ alkyl, substituted alkyl, or aryl;
Provided that $R_3$ and $R_4$ may not both be H;
$R_5$ is hydrogen, halogen, $C_1$–$C_4$ alkyl, substituted alkyl, —$OC_1$–$C_6$ alkyl, substituted —$OC_1$–$C_6$ alkyl, CN, $NO_2$, OH, —$N_3$, $NR_1R_2$, —$C(O)NR_1R_2$, —$C(S)NR_1R_2$, —O-aryl, or aryl; and pharmaceutically acceptable salts thereof.

46. A process for preparing a compound of claim 1 having the Formula 16

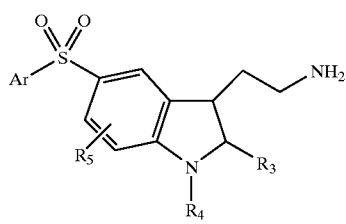

Formula 16 which comprises reducing a compound having the Formula 13

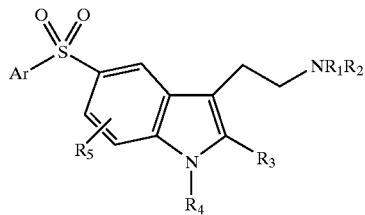

Formula 13 thereto, wherein

Aryl is phenyl, naphthyl, hetereoaromatic, substituted phenyl, substituted naphthyl, or substituted heteroaromatic;

$R_1$ is H, $C_1$–$C_6$ alkyl, substituted alkyl or aryl;

$R_2$ is H, $C_1$–$C_6$ alkyl, substituted alkyl or aryl;

$R_3$ is H, halogen, $C_1$–$C_6$ alkyl, substituted alkyl, or aryl;

$R_4$ is H, $C_1$–$C_6$ alkyl, substituted alkyl, or aryl;

Provided that $R_3$ and $R_4$ may not both be H;

$R_5$ is hydrogen, halogen, $C_1$–$C_4$ alkyl, substituted alkyl, —$OC_1$–$C_6$ alkyl, substituted —$OC_1$–$C_6$ alkyl, CN, $NO_2$, OH, —$N_3$, $NR_1R_2$, —$C(O)NR_1R_2$, —$C(S)NR_1R_2$, —O-aryl, or aryl; and pharmaceutically acceptable salts thereof.

* * * * *

UNITED STATES PATENT AND TRADEMARK OFFICE
CERTIFICATE OF CORRECTION

PATENT NO. : 6,565,829 B2 Page 1 of 1
DATED : May 20, 2003
INVENTOR(S) : Jian-Min Fu It is certified that error appears in the above-identified patent and that said Letters Patent is hereby corrected as shown below:

Column 39,
Line 37, please change "one of $R_1$ and $R^2$" to -- one of $R_1$ and $R_2$ --.

Signed and Sealed this

Second Day of December, 2003

JAMES E. ROGAN
*Director of the United States Patent and Trademark Office*